United States Patent
Wallace et al.

(10) Patent No.: US 11,197,755 B1
(45) Date of Patent: Dec. 14, 2021

(54) SYSTEMS, DEVICES AND METHODS FOR FOLDED UNIBODY HEART VALVE STENTS

(71) Applicant: Occam Labs LLC, Oakland, CA (US)

(72) Inventors: Daniel T. Wallace, Santa Cruz, CA (US); Jeremy J. Boyette, Woodside, CA (US); Peter W. Gregg, Santa Cruz, CA (US); Spencer C. Noe, San Miguel, CA (US); Evelyn N. Haynes, Los Gatos, CA (US)

(73) Assignee: Occam Labs LLC, Oakland, CA (US)

( * ) Notice: Subject to any disclaimer, the term of this patent is extended or adjusted under 35 U.S.C. 154(b) by 0 days.

(21) Appl. No.: 17/083,266

(22) Filed: Oct. 28, 2020

(51) Int. Cl.
*A61F 2/24* (2006.01)

(52) U.S. Cl.
CPC .......... *A61F 2/2418* (2013.01); *A61F 2/2436* (2013.01)

(58) Field of Classification Search
CPC ........ A61F 2/24; A61F 2/2409; A61F 2/2418; A61F 2/90; A61F 2250/0069; A61F 2/2427; A61F 2/2412; A61F 2/07; A61F 2/2469; A61F 2/82; A61F 2/86; A61F 2/246
See application file for complete search history.

(56) References Cited

U.S. PATENT DOCUMENTS

| | | | | |
|---|---|---|---|---|
| 2012/0191183 A1* | 7/2012 | Rzany | ................... | A61L 27/507 623/2.17 |
| 2014/0005778 A1* | 1/2014 | Buchbinder | .......... | A61F 2/2412 623/2.18 |
| 2014/0330370 A1* | 11/2014 | Matheny | ................ | A61F 2/2418 623/2.14 |
| 2014/0371844 A1* | 12/2014 | Dale | ..................... | A61F 2/2418 623/2.11 |
| 2015/0328002 A1* | 11/2015 | McLean | ................. | A61F 2/2427 623/2.36 |
| 2016/0030169 A1* | 2/2016 | Shahriari | .............. | A61F 2/2409 623/2.18 |
| 2016/0213826 A1 | 7/2016 | Tanner et al. | | |
| 2017/0100236 A1* | 4/2017 | Robertson | ............. | A61F 2/2418 |
| 2017/0128203 A1* | 5/2017 | Zhang | .................... | A61F 2/2439 |
| 2017/0216027 A1* | 8/2017 | Marchand | ............. | A61F 2/2436 |
| 2017/0325945 A1* | 11/2017 | Dale | ..................... | A61F 2/2418 |
| 2017/0325948 A1* | 11/2017 | Wallace | ............... | A61F 2/2409 |
| 2018/0021129 A1* | 1/2018 | Peterson | ............... | A61F 2/2412 623/2.17 |
| 2018/0116689 A1 | 5/2018 | Nakano | | |
| 2018/0206983 A1* | 7/2018 | Noe | ....................... | A61F 2/2445 |
| 2018/0256241 A1 | 9/2018 | Cohen et al. | | |
| 2020/0246527 A1 | 8/2020 | Hildebrand et al. | | |
| 2020/0405926 A1 | 12/2020 | Alexander et al. | | |
| 2021/0307943 A1* | 10/2021 | Gupta | ....................... | A61F 2/90 |

OTHER PUBLICATIONS

U.S. Appl. No. 17/179,308 titled "Systems, Devices and Methods for Delivery Systems" filed Feb. 18, 2021.

* cited by examiner

*Primary Examiner* — Seema Mathew
(74) *Attorney, Agent, or Firm* — Dorsey & Whitney LLP

(57) ABSTRACT

A replacement heart valve comprises a unibody, folded, double-wall stent, with a stent cover and a leaflet valve attached to the inner lumen of the stent. The heart valve is delivered using a multi-pulley, suture-based stent restraint assembly provided by fixed guide openings or structures along the distal end of the delivery system that independently permits expansion of the distal and proximal ends of the outer wall of the stent, and control of the inner wall expansion simultaneously with or separately from the expansion of the outer wall.

20 Claims, 21 Drawing Sheets

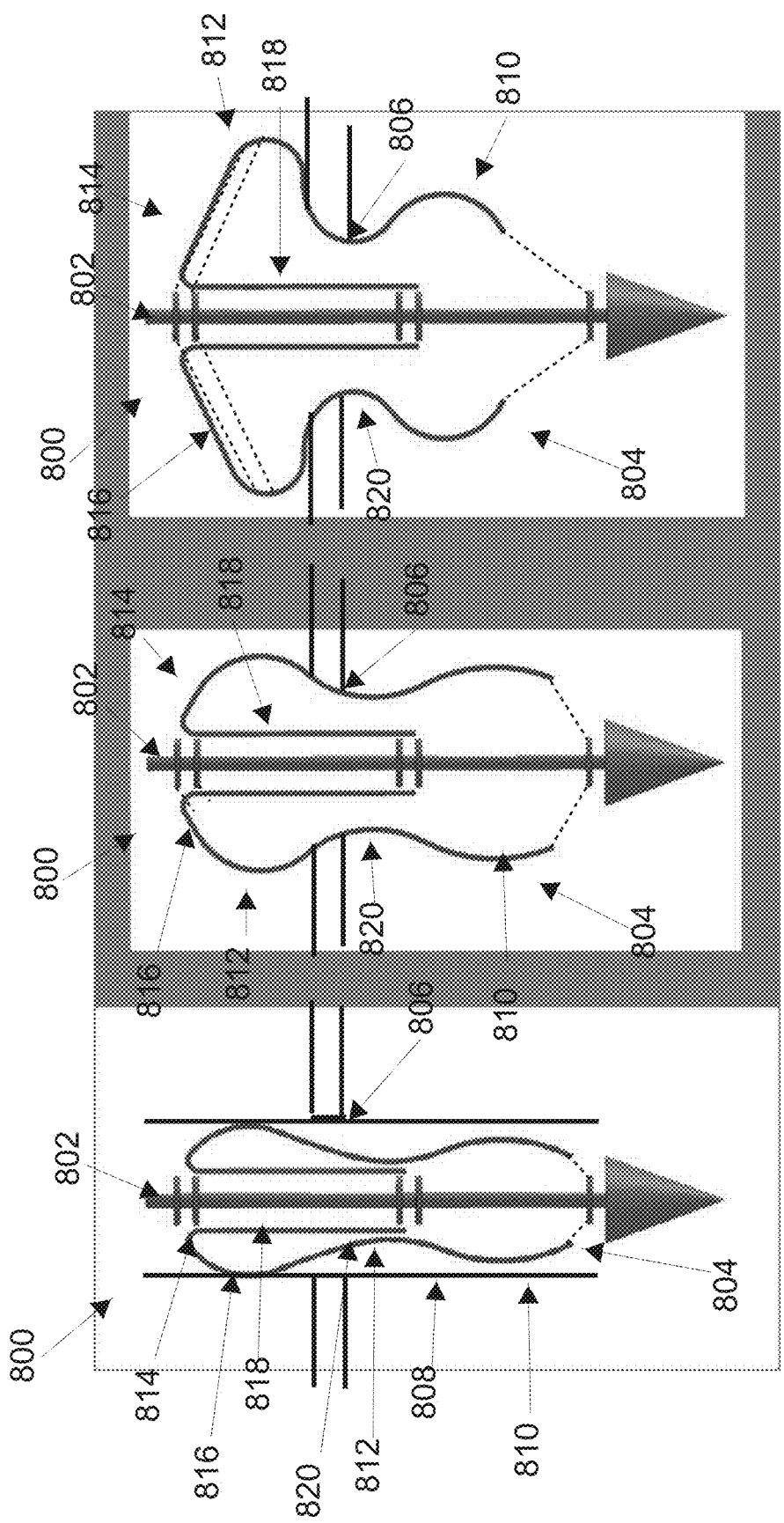

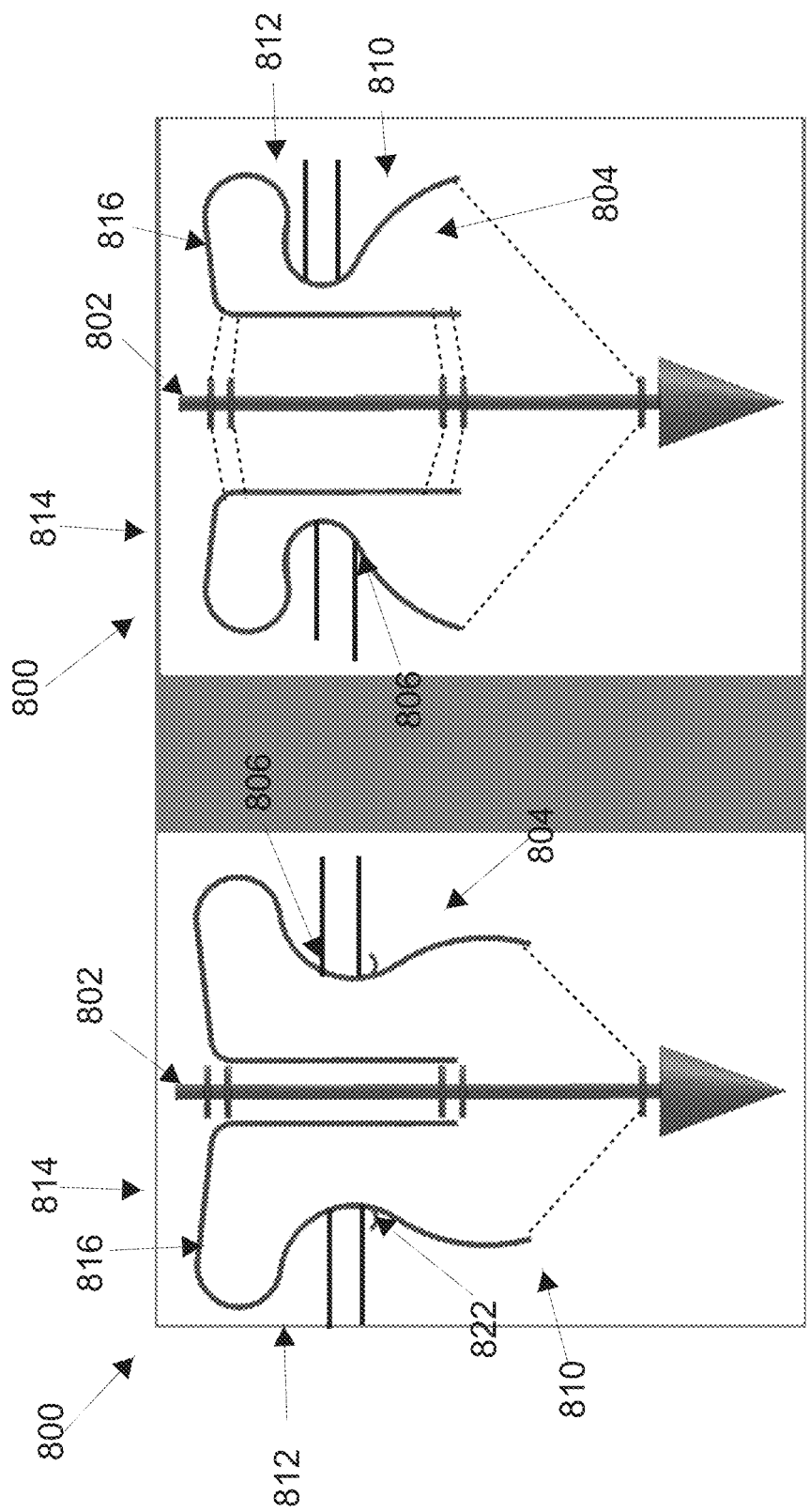

140
SYSTEMS, DEVICES AND METHODS FOR FOLDED UNIBODY HEART VALVE STENTS

BACKGROUND

This patent application relates generally to the treatment of valvular diseases, and more specifically to methods and apparatus for minimally invasive mitral valve replacement.

Valvular heart disease is a significant burden to patients and healthcare systems, with a prevalence of 2-3% worldwide, and with an increasing prevalence in aging populations. Valvular disease may result from a variety of etiologies, including autoimmune, infective and degenerative causes. The epidemiology of valvular disease also varies with the affected valve, with rheumatic heart disease being the cause worldwide of primary mitral regurgitation and mitral stenosis, but with secondary mitral disease from left ventricular dysfunction being more common in developed countries.

While surgical repair and valve replacement remains a mainstay of many mitral valve therapies in the current clinical guidelines by the American Heart Association and American College of Cardiology, transcatheter mitral repair is recommended for certain patient populations. In the 2017 Focused Update and the 2014 Guidelines for Management of Patients with Valvular Disease, the AHA/ACC recommended percutaneous mitral valve balloon commissurotomy for severe mitral valve stenosis, and transcatheter mitral valve repair in certain severely symptomatic patients with severe primary mitral regurgitation with a reasonable life expectancy who are non-surgical candidates due to comorbidities.

BRIEF SUMMARY

Further growth of transcatheter mitral valve therapies is challenged by the difficulty by mitral valve anatomy and physiology, compared to more established transcatheter aortic valve therapies. For example, some mitral valve replacement therapies in development make compromises between the sealing and anchoring properties of the outer portions of the replacement valve and the support of the leaflet valves. Other therapies attempt to address this challenge with two-part replacement valve structures, but these therapies may have high delivery failure rates or are too large for transcatheter delivery.

To address these issues, embodiments described herein are directed to a replacement heart valve comprising a unibody, folded, double-wall stent, with a stent cover and a leaflet valve attached to the inner lumen of the stent. The double wall stent structure decouples or reduces the effect on the geometry of the retention structure on the geometry of the valve support. This includes external forces acting through the valve annulus during the cardiac cycle, as well as the effect of non-circular valve annulus shapes. The double-wall stent structure also allows the valve support to have a different size and shape from outer annulus support, without having to conform to the native anatomy. This may reduce the risk of outflow track obstruction and/or impairment due to ventricular contraction, by permitting that the outer wall to have a shorter longitudinal length than the inner wall supporting the valve leaflets. The unibody design may also permit a greater structural integrity by reducing complications relating to force concentrations between joined, welded or mechanically connected support components and/or their attachment in situ.

In some variations, this permits the contraction of the expandable valve to a size of less than 29F, e.g. less than 10 mm, or between 24F and 29F, or between 8 mm and 10 mm. The heart valve may be delivered using a multi-pulley, suture-based stent restraint assembly on a catheter or delivery tool. Fixed guide openings or structures along the distal end of the delivery system that independently permits expansion of the distal and proximal ends of the outer wall of the stent via sutures passing through the openings. Control of the inner wall expansion may occur simultaneously with or occur independently from the expansion of the outer wall. The double-wall unibody design reduces the complexity over valves with multi-part structures while de-coupling the geometry of the valve support from the retention structure, while still providing a collapsibility suitable for transcatheter delivery.

In one example, a replacement heart valve is provided, comprising a unibody stent frame with a folded double-wall. The stent frame comprises a collapsed configuration and an expanded configuration, an outer wall comprising an open enlarged diameter region, a middle reduced diameter region, and a closed enlarged diameter region, a tubular inner wall with a central lumen, and a transition wall between the outer wall and inner wall, and a replacement leaflet valve located in the central lumen of the inner wall. The unibody stent frame may further comprises a first fold between the closed enlarged diameter region and the tubular inner wall. The unibody stent frame may further comprise a second fold between the closed enlarged region and the open enlarged region. The outer wall may surround at least 70 percent of the inner wall in the expanded configuration. The outer wall and transition wall may completely surround the inner wall in the collapsed configuration. The tubular inner wall may comprise a non-foreshortening region surrounding the replacement valve, when transitioning from the collapsed configuration to the expanded configuration. The inner wall may be a non-foreshortening inner wall, and the outer wall may be a foreshortening outer wall. The radius of curvature at the first fold may be smaller than the radius of curvature at the second fold. The unibody stent frame may also further comprise a plurality of longitudinal struts, wherein each longitudinal strut is contiguously located along the inner wall, transition wall and outer wall. In some variations, for at least one, or for all of the plurality of longitudinal struts, the contiguous segments of the longitudinal strut located in the inner wall, transition wall and outer wall are co-planar. The contiguous segments of the longitudinal strut may also be co-planar with the central longitudinal axis of the unibody stent frame. The plurality of longitudinal struts may be integrally formed with a plurality of circumferential struts. In some examples, at least three circumferential struts are located in the outer wall. The valve may also further comprise a stent covering, the stent covering comprising a first region on an outer surface of the outer wall, a second region on an open end of the outer wall, a third region on an outer surface of the transition wall, a fourth region on an inner surface of the inner wall, a fifth region on an open end of the inner wall, a sixth region on an outer surface of the inner wall, a seventh region on an inner surface of the outer wall, and an eighth region portion between the inner surface of the outer wall and the outer surface of the inner wall. The first, second, third, and a portion of the fourth regions may comprise a first fabric structure, a portion of the fourth region and the fifth region may comprise a second fabric structure and the sixth, seventh and eighth regions may comprise a third fabric structure. The first fabric structure and the third fabric structure may comprise a first fabric material and the second fabric structure may comprise a second fabric material different from the first fabric material. The first fabric material may be less permeable and thinner than the second fabric material. The plurality of longitudinal struts and the plurality of circumferential struts may comprise a segmented annular cross-sectional shape, and wherein an orientation of the segmented annular cross-sectional shape in the inner wall is opposite of an orientation of the segmented annular cross-sectional shape in the outer wall.

In another embodiment, a replacement heart valve is provided, comprising a unibody stent frame with a folded double-wall, the stent frame comprising, an outer wall comprising an open enlarged diameter region, a middle reduced diameter region, and a closed enlarged diameter region, a cylindrical inner wall with a central lumen and a transition surface between the outer wall and inner wall; and a replacement leaflet valve located in the central lumen of the inner wall. The unibody stent frame may further comprise a plurality of longitudinal struts, wherein each longitudinal strut comprising a longitudinal outer wall segment that is contiguous with a transition surface segment and a longitudinal inner wall segment. For at least one of the plurality of longitudinal struts, the longitudinal outer wall segment, the transition surface segment and longitudinal inner wall segment may be contiguously co-planar. The unibody stent frame may comprises a central longitudinal axis, and wherein the contiguously co-planar longitudinal outer wall segment, transition surface segment, longitudinal inner wall segment of each of the at least one of the plurality of longitudinal struts are also co-planar with the central longitudinal axis. In some examples, adjacent longitudinal struts of the plurality of longitudinal struts may be circumferentially formed with a plurality of chevron struts. Each of the plurality of longitudinal struts may comprise a longitudinal outer wall segment, a transition surface segment, and a longitudinal inner wall segment that is contiguously co-planar. The unibody stent frame may have a relatively smaller radius of curvature at a transition junction between the outer wall and transition surface, and a relatively larger radius of curvature at a transition junction between the transition surface and the inner wall.

In still another example, a stent may be provide, comprising a unibody double-wall expandable stent frame with a central opening and central axis, and comprising an expanded configuration and a contracted configuration. The stent frame may be a folded stent frame. The folded stent frame may be an everted or inverted stent frame. The stent frame may further comprises a circumferential inner wall, the inner wall comprising an open end, a transition end, and inner and outer surfaces therebetween, a circumferential outer wall, the outer wall comprising an open end, a transition end, and inner and outer surfaces therebetween, and a transition wall between the transition ends of the inner and outer walls. The inner wall of the stent frame may be non-foreshortening in the expanded configuration relative to the contracted configuration. The stent frame may further comprise an annular cavity between the inner wall and outer wall, the cavity comprising an annular closed end at the transition wall and an annular open end between the open ends of the inner and outer walls. The outer wall may comprises a middle region with a reduced cross-sectional area in the expanded configuration, relative to the cross-sectional area at an end region of the outer wall. The inner wall may comprise a cylindrical or frustoconical shape. In the contracted configuration, the inner surface of the outer wall may be spaced closer to the outer surface of the inner wall, and wherein the expanded configuration, the inner surface of the outer wall is spaced longitudinally distal from the outer surface of the inner wall relative to the contracted configuration. The stent frame may further comprise a first delivery configuration wherein the transition ends of the inner and outer walls are in a partially expanded configuration and the open ends of the inner and outer walls are in a partially contracted configuration. The transition wall may have a transverse orientation relative to the central axis in the expanded configuration, and a longitudinal orientation relative to the central longitudinal axis and a radially outward location relative to the inner wall in the contracted configuration. The stent frame may have a smaller radius of curvature at the transition end of the outer wall, relative to a larger radius of curvature at the transition end of the inner wall, or may have a larger radius of curvature between the open end and the transition end of the outer wall, relative to the smaller radius of curvature at the transition end of the outer wall. The stent frame comprises a plurality of longitudinal struts, wherein each longitudinal strut comprising a longitudinal outer wall segment that is contiguous and radially aligned with a longitudinal inner wall segment via a transition wall segment. The adjacent longitudinal struts of the plurality of longitudinal struts may be circumferentially spaced apart via a plurality of chevron struts. Each chevron strut of the plurality of chevron struts may comprise first and second legs, with each leg comprising a base end integrally formed with one of the adjacent longitudinal struts, and a distal end integrally formed with the distal end of the other leg. The integrally formed distal ends of the first and second legs may comprises a hairpin configuration. At least some of the plurality of chevron struts may be oriented in a tangential plane defined by adjacent longitudinal strut segments about which each chevron strut is integrally formed. At least one of the plurality of chevron struts may be oriented radially out-of-plane from the tangential plane. The out-of-plane chevron strut may be integrally formed with adjacent longitudinal struts in the outer wall and wherein the hairpin configuration projects into a reduced diameter region of the stent frame and points toward the transition end of the outer wall. In some variations, the may further comprise a leaflet valve sutured to the inner wall. The plurality of chevron struts may comprises a plurality of undulating circumferential struts. The stent may further comprise a first fabric covering that comprises an outer cuff covering a portion of the outer surface of the outer wall, the open end of the outer wall, and a portion of the inner surface of the outer wall and a second fabric covering that covers a portion of the outer surface of the outer wall, the transition wall and a portion of the inner surface of the inner wall. The open end of the inner wall may be offset from the open end of the outer wall along the central longitudinal axis.

In still another embodiment, a replacement heart valve is provided, comprising a unibody stent frame with a folded double-wall hourglass shape, the stent frame comprising an outer wall with an hourglass shape, the hourglass shape comprising an open enlarged diameter region, a middle reduced diameter region, and a closed enlarged diameter region, a non-foreshortening tubular inner wall with a central lumen, and a transition wall between the outer wall and inner wall, and a replacement leaflet valve located in the central lumen of the inner wall.

In another example, a method for using a heart valve delivery system is provided, comprising inserting a delivery catheter through a valve and a central opening of a unibody folded double wall valve frame, releasably attaching a first retention assembly to an inner wall of the valve frame, releasably attaching a second retention assembly to an outer wall of the valve frame, tensioning the first retention assembly to collapse the inner wall of the valve frame onto the delivery catheter, and tensioning the second retention assembly to collapse the outer wall of the valve frame onto the inner wall of the valve frame. The collapsing of the outer wall of the valve frame may comprises distally tensioning, stretching or pulling the outer wall of the valve frame toward a distal end of the catheter. The method may further comprise sliding a delivery sheath of the delivery catheter over the collapsed valve.

In another example, a method for performing mitral valve replacement is provided, comprising positioning a delivery device containing a collapsed heart valve assembly in an orthogonal, centered pose across the native mitral valve, wherein the heart valve assembly comprises a unibody folded stent and attached valve leaflets, retracting a sheath of the delivery device to expose the collapsed heart valve, expanding an atrial end of an outer wall of the unibody folded stent in the left atrium, expanding a ventricular end of the outer wall of the unibody folded stent in the left ventricle, expanding the inner wall of the unibody folded stent, and releasing the unibody folded heart valve from the delivery device. The method may further comprise accessing a femoral vein, inserting a transseptal puncture device through the femoral vein and to the right atrium, puncturing the intraatrial septum, and inserting the delivery device with a collapsed heart valve assembly through the femoral vein and into the left atrium. In some further examples, expanding the atrial end of the outer wall and expanding the ventricular end of the outer wall may occur at least partially simultaneously. Expanding the atrial end of the outer wall and expanding the inner wall may also occur at least partially simultaneously. The method may also further comprise dilating the intraatrial septum. Alternatively, the method may further comprise accessing the left thoracic cavity through the chest wall, puncturing the cardiac tissue at an apex of the left ventricle, and inserting the delivery device with a collapsed heart valve assembly though the chest wall and transapically into the left ventricle. With the latter method, an open end of the unibody folded stent may have a proximal location on the delivery device relative to a transition end of the unibody fold stent having a distal location on the delivery device. Still another further embodiment, the method may further comprise accessing a femoral artery and inserting the delivery device with a collapsed heart valve assembly through the femoral artery and aortic arch and into the left ventricle.

BRIEF DESCRIPTION OF THE DRAWINGS

FIG. 1F is a schematic cross-sectional view of FIG. 1B.

FIGS. 8A to 8E are schematic cross-sectional views of an exemplary views of a deployment procedure for a heart valve stent and delivery system.

DETAILED DESCRIPTION

Figure 1A:
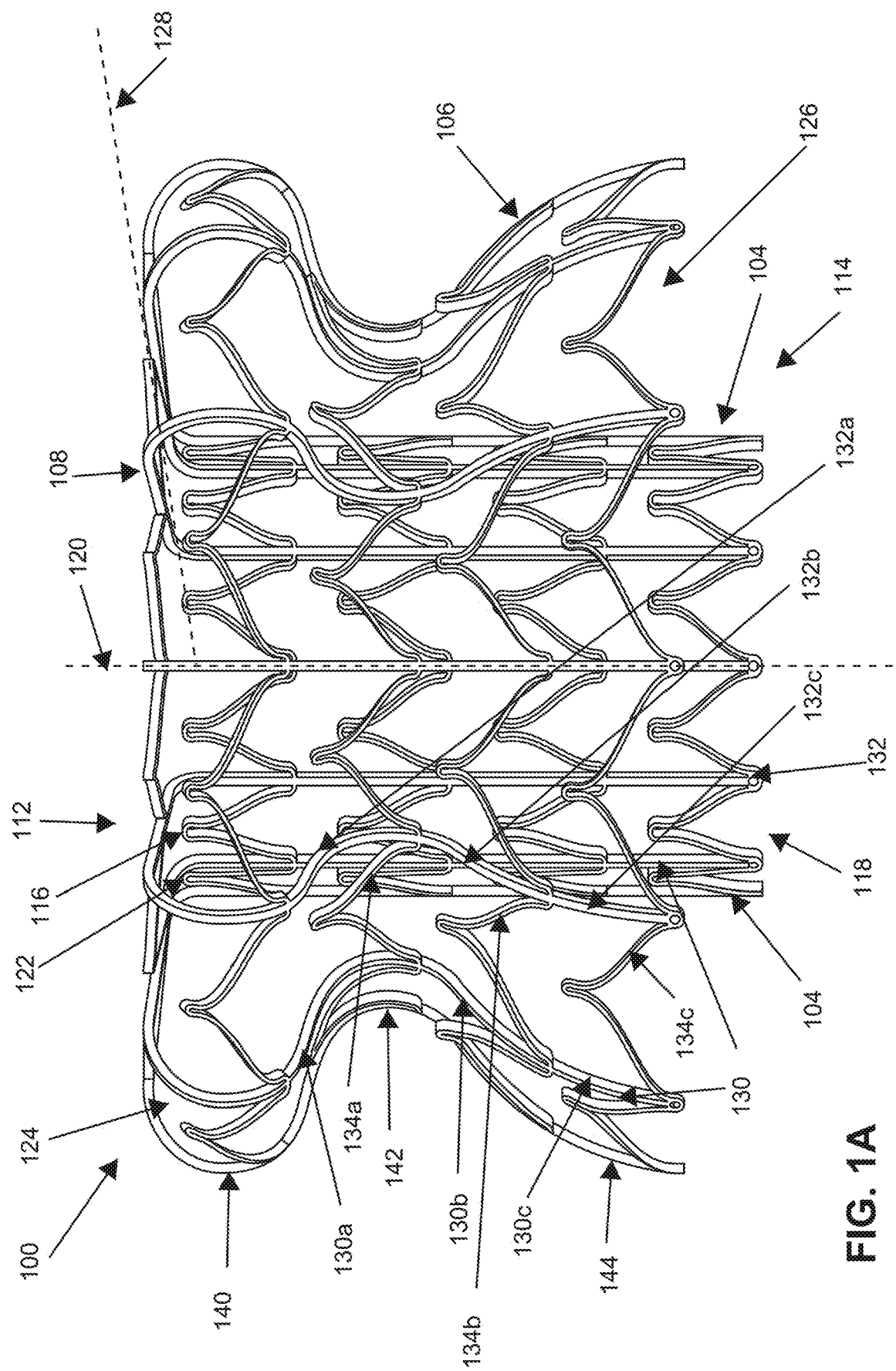
FIGS. 1A and 1B are schematic side elevation and top plan views of one embodiment of a heart valve stent.
Figure 1B:
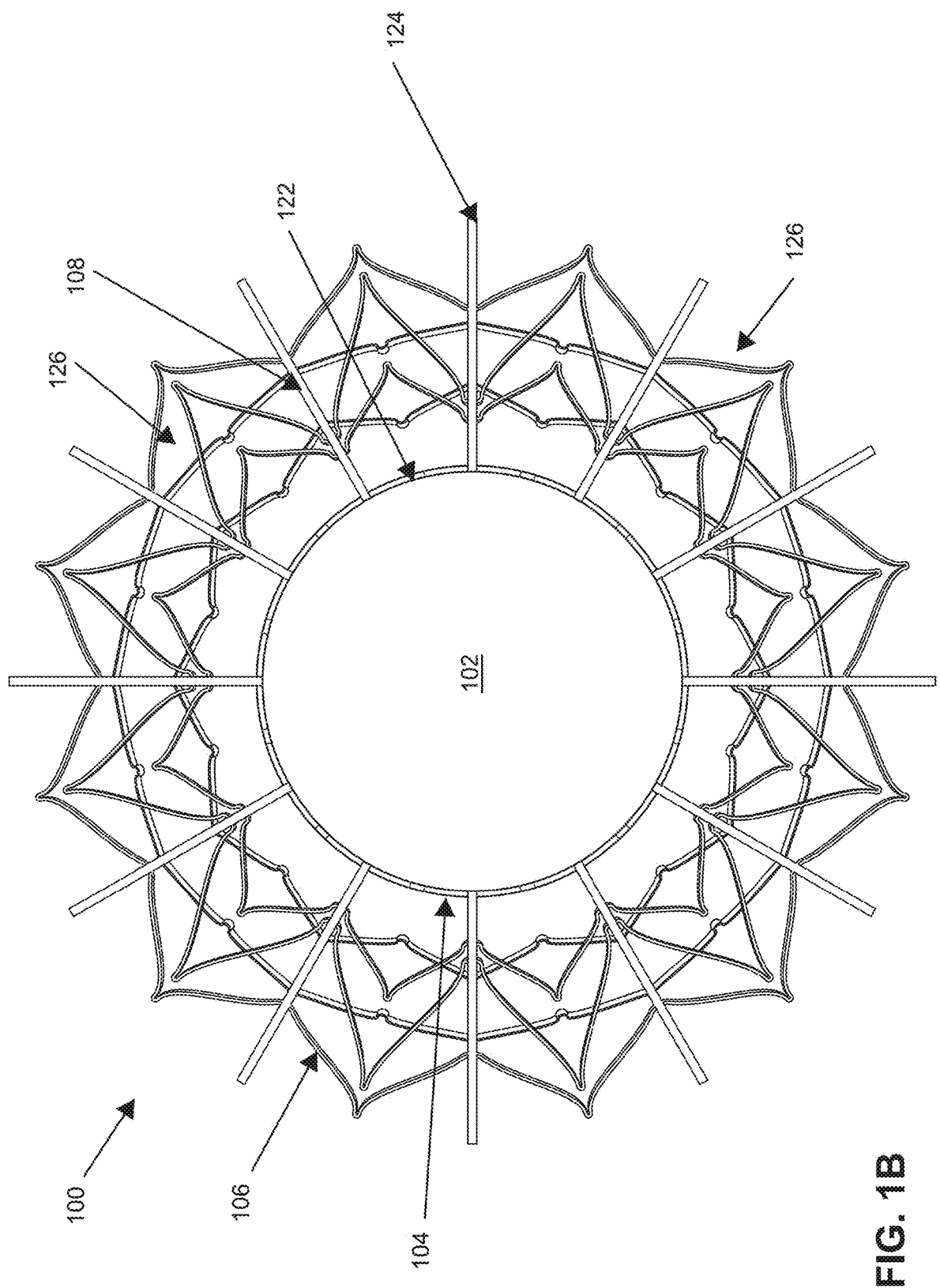

The embodiments herein are directed to a double-wall, folded stent structure with an inner wall providing a tubular lumen that is attached to a leaflet valve assembly. The inner wall is spaced apart from a tubular outer wall that is configured to seal and/or anchor to the surround native valve anatomy, but is contiguous with the inner wall via a transition wall. The transition wall may result from the folding, inversion or eversion of a single tubular structure into a double-wall unibody tubular stent frame or structure. The stent is configured to reversibly collapse into a reduced diameter or reduced cross-sectional shape for loading into a catheter and for delivery to a target anatomical site, and then to re-expand at the implantation site.

In further embodiments, the folded stent structure may be shaped with a middle region having a reduced cross-sectional size in the outer wall, which may facilitate anchoring of the structure across the desired anatomical site. The middle region with the reduced diameter or dimension is configured to expand against the native valve leaflets and/or anatomical orifice, while the enlarged diameter or dimensions of the end regions provide mechanical interference or resistance to displacement. The transition wall of the stent structure may be configured to facilitate inflow of fluid into the inner lumen and through the replacement valve leaflets, while reducing turbulence and/or hemodynamic forces that may displace or dislodge the valve. For example, the transition wall may be angled or tapered radially inward from the outer wall to the inner wall, to improve flow or decreased peak forces acting on the transition wall, compared to a transition wall that is orthogonally oriented between the outer wall and inner wall, or to the longitudinal axis of the stent structure.

Although some of the exemplary embodiments described herein are directed to transcatheter replacement of mitral valves, the components and structures herein are not limited to any specific valve or delivery method, and may be adapted to implantation at the tricuspid, pulmonary, aortic valve locations, and also in non-cardiac locations, e.g. the aorta, venous system or cerebrospinal fluid system, or a native or artificial conduit, duct or shunt. As used herein, the spatial references to a first or upper end of a component may also be characterized by the anatomical space the component occupies and/or the relative direction of fluid flow. For example, the first or upper end of folded stent structure of a replacement mitral valve may also be referenced as the atrial end or upstream end of the valve, while the opposite end may be referenced as the ventricular end or downstream end of the valve.

An exemplary embodiment of a stent structure 100 are depicted in FIGS. 1A-1G, in their expanded configuration. The stent structure 100 comprises an inner lumen 102 formed by an inner all 104. An outer wall 106 is spaced radially apart from the inner wall 104 via a transition wall 108, and forms an annular cavity 110. The stent structure 100 has first closed end 112 that is located at the transition wall 108, and a second open end 114 of the outer wall 106, wherein the annular cavity 110 is open and accessible.

The inner lumen 102 comprises a first opening 116 surrounded by the transition wall 108 and a second opening 118 at the second open end 114 of the stent structure 100. The longitudinal axis 120, 320 of the inner lumen 102 is typically coincident with the central axis of the stent structure 100, but in some variations, the inner lumen may be eccentrically located relative to the outer wall of the stent structure. The inner lumen 102 typically comprises a circular cross-sectional shape with a generally cylindrical shape between the first opening 116 and second opening 118, as depicted in FIGS. 1A to 1D. In other examples, the inner lumen may comprise a frustoconical, oval or polygonal shape. In some variations, the stent structure may comprises an inner lumen where the size and/or shape of the first and second openings may be different. The lengths of the inner lumen 102 may be in the range of 10 mm to 50 mm, 15 mm to 40 mm, or 20 mm to 25 mm, and the diameter or maximum cross-sectional dimension of the inner lumen along its longitudinal length may be in the range of 15 mm to 40 mm, 20 mm to 30 mm, or 25 mm to 30 mm. In embodiments where the inner lumen comprises a non-cylindrical shape, the difference between the diameter or cross-sectional dimension of the first opening 116 and the second opening 118 may be in the range of 1 mm to 10 mm, 1 mm to 5 mm, or 1 mm to 3 mm.

The location of the first and second openings 116, 118 of the inner lumen 102 relative to the overall stent structure 100 may also vary. In some variations, the first opening 116 of the inner lumen 102 may be recessed relative to the first end 112, as depicted in FIGS. 1A to 1G. In other examples, the first opening may be generally flush with the first end and transition wall of the stent structure. The location of the first opening 116 may also be characterized as recessed, flush or protruding relative to the longitudinal location of the inner junction 122 between the inner wall 104 or lumen 102 and transition wall 108, or relative to the outer junction 124 between the transition wall 108 and the outer wall 106, as depicted in FIG. 1G. Likewise, the second opening 118 of the inner lumen 102 may also be characterized as recessed, flush or protruding, relative to the longitudinal location of outer opening 126 of the outer wall 106. For example, with stent structure 100, the second opening 118 of the inner lumen 102 comprises an offset or protruding location relative to the outer opening 126 of the outer wall 106. In some variations, the inner lumen may protrude relative to the second opening of the outer wall in variations where a smaller or shorter outer wall is preferred to accommodate smaller size native valve anatomy. The inner lumen size, however, may remain relatively the same size between different size variations, to provide consistent valve geometry and/or hemodynamic characteristics.

The transition wall 108 of the stent structures 100 has a generally annular and slightly tapered shape surrounding the inner lumen 102 in the expanded configuration, but in other variations may have a different shape and/or surface angle. Referring to FIG. 1G, for example, the transition walls 108 on cross section may comprise a generally linear shape between the inner junction 122 and the outer junction 124, but in other variations, may comprise a curved shape, e.g. concave or convex shape. In other variations, the transition wall may have a generally orthogonal angle relative to the longitudinal axis of the inner lumen. Referring back to FIG. 1G, the transition walls 108 of stent structure 100 may form an external acute angle 128 relative to the longitudinal axes 120 of the inner lumen 102. The angle 128 may be in the range of +45 to +89 degrees, +75 to +89 degrees, or +81 to +85 degrees, with optional variances in the range of ±1 degree, ±2 degrees, ±3 degrees or ±4 degrees. In other variations, the transition wall angles may be in the range of −45 to +45 degrees, −75 to +75 degrees, or −85 to +85 degrees.

As noted previously, in some embodiments, the outer wall 106 of the stent structure 100 comprises a non-cylindrical shape when in the expanded configuration. The outer wall 106 may comprise a first end region 140 that is contiguous with the transition wall 108, comprising an external convex shape, a second end region 142 that forms the outer opening 126, As shown, the inner junction 122 between the upper region of inner wall 104 and the transition wall 108 may comprise a first or upper inner radius of curvature $R_1$ along the inner curvature of the bend, and a first or upper inner bend angle $A_1$. The bend angle is the angle defined by the arc length of the bend from the center of the radius of curvature, between points where the bend transitions to a linear segment or a different bend. The outer junction 124 between the transition wall 308 and the upper region of the outer wall 106 may comprise a second or upper outer radius of curvature $R_2$ and a second or upper outer bend angle $A_2$. The middle region of the outer wall 108 comprises a third or middle radius of curvature $R_3$ and a third or middle bend angle $A_3$, and the lower region of the outer wall 108 may comprise a fourth or lower radius of curvature $R_4$ and fourth or lower bend angle $A_4$.

As shown in FIG. 1G, the centerpoints of the first and second radii of curvatures $R_1$, $R_2$ lie may lie within the annular cavity 110 of the stent 100, while the third radii of curvature $R_3$ may be external to the outer wall 108, and the fourth radii of curvature $R_4$ may be in the ipsilateral annular cavity 110, the inner lumen 102, the contralateral annular cavity 110$b$, depending on the size.

The radii of curvature and the bend angles of the stent structure may be used to define the geometry of the stent in the expanded configuration, but also affect the geometry of the stent in its delivery or collapsed configuration. Regions or segments of the stent may be configured with a smaller radius of curvature and/or larger bend angle to facilitate the folding of the stent at that region or segment as the stent is collapsed for the delivery or collapsed configuration. A larger radius of curvature or a smaller bend angle may be provided to facilitate straightening of that region or segment for the delivery or collapsed configuration. For example, with stent structure 100, a relatively smaller radius of curvature $R_1$ facilitates the folding or collapse of the stent structure at the inner junction 122, while a larger radius of curvature $R_2$ facilitates the flattening of the first end region 140 during delivery or loading of the device into the delivery system. Thus, in the collapsed configuration, the transition wall 108 is further bent at the inner junction 122 and collapsed around the inner wall 104. The outer wall 106 is also collapsed around the inner wall 104, but not collapsed around the transition wall 108 Similarly, the middle region 142 and second end region 144 of the outer wall 106 may also be provided with a larger radius of curvature $R_3$ and $R_4$, which will result in flattening of the concave shape in the middle region 142 and convex shape of the second end region 144 to also facilitate collapse of the outer wall 106. Thus, for stent 100 in its collapsed configuration, the inner wall 104 will be radially inward to the outer wall 106 and to the transition wall 108. The outer wall 106 and transition wall 108 will be in contact with a sheath, capsule or outer wall of a delivery system, while the inner wall 104 may be in contact with an inner core or inner catheter wall. In other embodiments, the stent structure may be provided with a relative larger radius of curvature $R_1$ and smaller radius of curvature $R_2$, such that in the collapsed configuration, the transition wall will collapse proximally against the delivery device and not the inner wall 104, and where the outer wall 106 is collapsed against both the inner wall 104 and the transition wall 108.

In some variations, the stent geometry may be characterized by one or more relative characteristics of the stent in its expanded configuration. For example, stent 100 may be characterized as $A_3 > A_1$ and $A_3 > A_2$ $_{and}$ $A_3 > A_4$ and/or $R_1 < R_2 < R_3 < R_4$, $R_1 < R_2 \approx R_3 < R_4$ $R_1 < R_2 \approx R_3 \approx R_4$, or $R_1 \leq R_2 \leq R_3 \leq R_4$.

Other stent variations may include:
1) $R_2 < R_1 < R_3 < R_4$;
2) $R_2 < R_1 \approx R_3 < R_4$;
3) $R_2 < R_1 \approx R_3 \approx R_4$;
4) $R_4 > R_1 \approx R_2$;
5) $R_4 > R_1 \approx R_2 > R_3$;
6) $A_2:A_1$ ratio in the range of 1 to 3, 1.5 to 2.5 or 1.8 to 2.2;
7) $A_3:A_4$ ratio in the range of 1 to 4, 1.5 to 3.0 or 2.2 to 2.4;
8) $A_2:A_4$ ratio in the range of 2 to 4, 2.5 to 3.5 or 2.8 to 3.2;

The stent structures herein further comprise a plurality of integrally formed stent struts segments, as depicted in FIGS. 1A to 1G. Some struts may be characterized as longitudinal strut segments 130a, 130b, 130c which generally reside within a radial plane in which the longitudinal axis of the stent structure also resides, or lateral strut segments 134a, 134b, 134c, which are integrally formed with longitudinal struts 130a, 130b, 130c, 132a, 132b, 132c, where the two longitudinal struts 130, 132 are lying in different adjacent radially oriented planes, respectively. In embodiments with an even number of equally spaced apart longitudinal struts, as depicted in FIG. 1G, each radial plane 150 will include the longitudinal axis 120 of the stent structure 100, and two longitudinal struts 130, 136 located on opposite sides of the stent structure 100. The longitudinal and lateral strut segments may also be further grouped, with a group of longitudinal strut segments lying in the same radial plane to form a contiguous length of longitudinal strut 130, 132 in the inner wall 104 transition wall 108 and/or outer wall 106.

In some examples, a longitudinal strut, comprising a plurality of contiguous longitudinal strut segments, provided in one wall may terminate or be interrupted at the junction of the next wall, but in some embodiments, may span the two or three walls. In some further embodiments, a longitudinal strut may be provided along the entire folded length of a stent structure, between the opening of the inner lumen, along the length of the inner wall and through the transition and outer wall to the end of the outer wall, while still having each of the contiguous strut segments residing in the same radial plane 150, as depicted for longitudinal struts 130, 152 in FIG. 1G. It is hypothesized that such an arrangement of the multiple contiguous longitudinal struts throughout the folded stent structure provides a structural integrity to the stent structure that better redistributes forces acting on the stent structure, with less force concentration found in stent structures that comprises multiple components that are welded or attached together, whether at the point of manufacture or at the point of use. In still other examples, the contiguous length of longitudinal struts may span all three walls but the stent may comprise a different strut configuration at one or both of the inner and outer ends of the folded stent structure, e.g. different orientation of circumferential struts or tissue anchors.

In exemplary stent structure 100, the longitudinal strut segments along the inner lumen of the stent structure 100 comprise a linear configuration, so the longitudinal strut segments are generally parallel in both their expanded and contracted configurations. Because of this arrangement, the inner lumen 102 do not exhibit any foreshortening when changing from the contracted to the expanded configuration. This may reduce or eliminate any axial stretching of the valve structure attached to the inner lumen. This may also permits the inner lumen to be predictably positioned and deployed while reducing the risk of inadvertent position shifting.

While the non-cylindrical configuration of the outer wall 106 may exhibit some foreshortening as the outer wall 106, transitions from a relatively straight orientation in the contracted configuration to the convex/concave/convex orientation in its expanded configuration, the foreshortening effect or displacement of net displacement of a region of the stent structure from the contracted to the deployed configuration may be controlled or limited by the change in the orientation of the transition wall 108 which can displace the outer wall 106 toward the open end of the stent structure 100 and offset some of the other displacements of the outer wall such that the reduced diameter middle section of the outer wall is generally maintained in the contracted and expanded configurations. In some variations, the longitudinal shift upon expansion of the stent structure in the reduced diameter middle section of the outer wall may be less than 5 mm, 4 mm, 3 mm, 2 mm, or 1 mm.

The lateral strut segments may also be characterized by a contiguous set of lateral strut segments that form a partial or complete circumferential or perimeter strut around a wall of the stent structure. The lateral strut segments, however, can vary in more than just their circumferential orientation. To facilitate the expansion and contraction of the overall stent structure, one or more of the lateral strut segments, or all of the strut segments, may comprise a pair of angled legs, each lateral end of each angled leg is contiguous or integrally formed with a longitudinal strut segment or strut and where each angled leg is joined together centrally. While the bend configuration of the formed by the two angled legs may comprise a simple bend, in other examples, each leg may extend centrally to form a hairpin bend region.

Figure 4A:
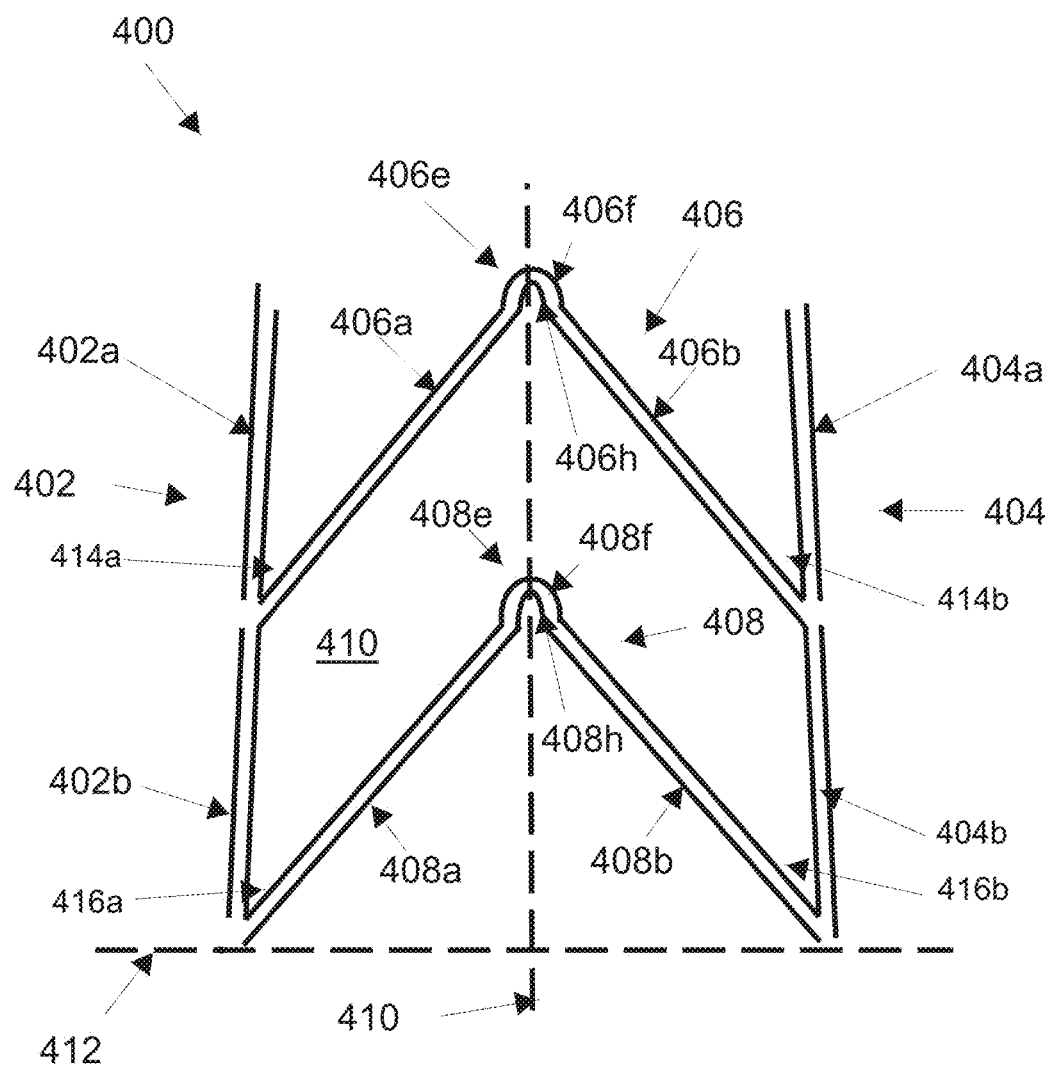
FIGS. 4A to 4C depict various exemplary strut configurations.
Figure 4B:
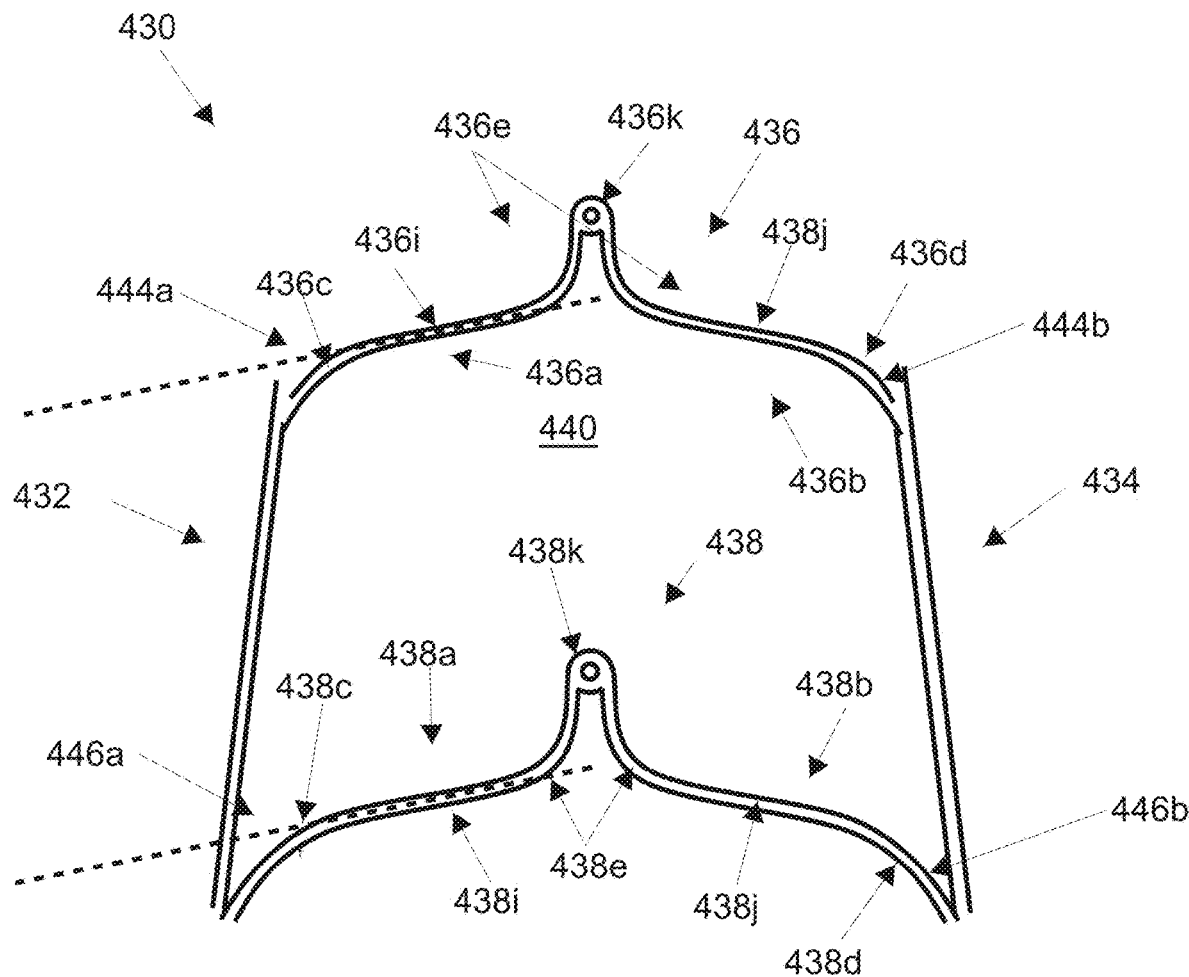
Figure 4C:
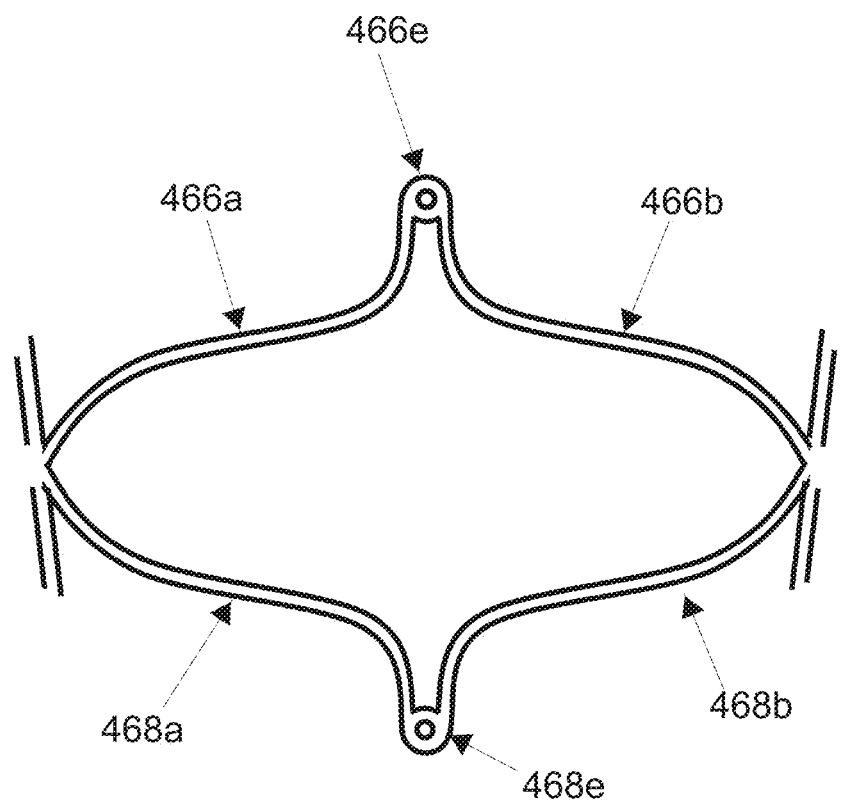

The leg angle formed between each leg and the longitudinal strut may vary in different regions of the stent structure, and may vary depending on the leg length. In FIG. 4A, an exemplary configuration of the lateral strut segment in the inner wall of the stent structure is depicted. Because of the relative lower amount of radial expansion that is exhibited by the inner wall compared to the outer wall, in the expanded configuration the leg lengths of the inner wall are typically shorter than the leg lengths found in the outer wall. Also, due to the limited radial expansion, the legs in the inner wall may have a generally linear configuration, since the structure strain generated at the leg angle is limited. Referring to FIGS. 4B and 4C, in other regions of the stent structure, where a greater amount of radial expansion is experienced, e.g. the outer wall and potentially the transition wall, each leg may comprise a convex curvature along the acute leg angle and a concave curvature along the acute leg angle closer to the middle bend region.

In some embodiments, the lateral strut segments in the inner wall may comprise an acute leg angle that is less than 50 degrees, 45 degrees or 40 degrees, or in the range of 30-50 degrees, 35-45 degrees, or 35-40 degrees, while the acute leg angle in the outer wall may be in the range of 30-75 degrees, 30-60 degrees, 35-55 degrees, or 40-50 degrees. The longitudinal spacing between longitudinally adjacent lateral strut segments in the inner lumen may be smaller than the longitudinal spacing in the outer wall, e.g. 2-8 mm, 3-7 mm, 4-6 mm, 2-6 mm, or 3-5 mm for the inner wall, and 4-10 mm, 5-10 mm, 6-9 mm. This spacing is also the length of the longitudinal strut segments in the various wall regions.

Referring to FIG. 1G, the orientation of the legs and middle bends of one or more set of circumferential strut segments may also deviate radially outward relative to the adjacent longitudinal struts to provide barb-like or force concentration structures to resist displacement of the strut structure relative to the native valve tissue. The lateral struts configured with barbs may be located anywhere along and/or around the outer wall of the stent structure, but in some variations, may be located in the outer wall regions 142 and 144, between the reduced diameter region 142 and the outer opening 126 of the stent structure 100, and oriented toward the reduced diameter region 142. In some further examples, the radially outward displaced circumferential struts may be provided at one or more circumferential struts that are closest to and point toward the region of the outer wall with the smallest diameter. In variations of valves used for mitral valve replacement, the barbs may be formed in the struts to engage the sub-annular tissue on the ventricular side. In some examples, every lateral strut segment in a circumferential strut is radially displaced, but in other examples, 2, 3, 4, 5, 6, 7, 8, 9, 10, 11, 12 or any range between any two of these numbers may radially displaced, or every other or every third or fourth lateral strut segment may be radially displaced. The degree of projection from outer wall shape defined by the plurality of longitudinal struts may be in the range of 2-10 mm, 2-6 mm, or 2-4 mm. In some variations, the barb configuration may be characterized by the ratio of the radial distance between the barb tip and the longitudinal axis of the stent structure, and the radial distance between an adjacent longitudinal strut or outer wall segment (excluding the barb) and the longitudinal axis of the stent structure. This ratio may be in the range of 1.1 to 1.5, 1.05 to 1.30, or 1.10 to 1.20.

In some further examples, control apertures or attachment structures may be provided on a strut segment or at the junction between two or more strut segments. The control aperture may be used to releasably attach tensioning members, including but not limited sutures, wires and hooks, which may be relaxed or tensioned to control the expansion, contraction, release or loading of the stent structure during delivery of the valve prosthesis or loading of the valve prosthesis into its delivery system. Various embodiments of the delivery system and method are described in greater detail below. Referring to example in FIG. 1E, control apertures are optionally provided at the junction of the end of each contiguous longitudinal strut in the outer wall and in the inner wall. In addition, control apertures may be option-ally provided in the middle bends of one or both of the two circumferential struts closest to the outer opening 126 of the outer wall 106.

FIG. 4A schematically depicts one example of a strut configuration 400 that may be provided on a region or wall of a stent structure. The strut configuration 400 comprises longitudinal struts 402, 404 and lateral struts 406, 408. Longitudinal strut segments 402a, 404a and lateral strut segments 406,408 together form a closed perimeter of a stent opening or cell 410. For purposes of characterizing various geometrical configurations of the strut configuration, a longitudinal axis 410 and a transverse axis 412 are described herein, but a person of skill in the art will understand that other reference points or axis may be also be used. Longitudinal axis 410 that is parallel to the longitudinal axis of the overall stent structure, while transverse axis 412 is orthogonal to the longitudinal axis 412.

In the schematic strut configuration 400 depicted in FIG. 4A, the longitudinal struts 402, 404 may be parallel or non-parallel, depending on whether the inner lumen comprises a cylindrical or non-cylindrical shape, e.g. a frusto-conical shape. In variations, where the longitudinal struts are non-parallel, the longitudinal struts 402, 404 may have a small radial angle orientation about 1-5 degrees, 2-10 degrees, or 5 to 30 degrees from the longitudinal axis of the stent structure, so as to provide a frustoconical shape. As depicted in FIG. 4A, the longitudinal and lateral struts 402, 404, 406, 408 may comprise strut segments 402a, 402b, 404a, 404b, 406a, 406b, 408a, 408b. In some variations, the inner walls 104 of stent structures 100, the legs 406a, 406b, 408a, 408b of lateral struts 406, 408 may comprise a generally linear or straight configuration, with deformations occurring primarily at the base 406c, 406d, 408c, 408d and the bend region 406e, 408e of each lateral strut 406, 408. In some variations, where greater rigidity is desired, the lateral struts may be generally non-uniform along its length. This would be achieved by increasing the relative width near the base of the strut and decreasing the relative width in the mid-portion of the strut. The acute angle 414a, 414b, 416a, 416b between the longitudinal struts 402, 404 and the legs 406a, 406b, 408a, 408b in this strut configuration 400 may be in the range of 1-45 degrees, 10-40 degrees, or 20-35 degrees. In some variations, the middle region where the pairs of legs are integrally formed may comprise a simple angle or curved configuration, but in other variations, may comprise bend regions 406e, 408e, with arcuate structures having a greater curvature 406f, 408f on the same side as the acute angle of the lateral strut, and the lesser curvature 406g, 408g found on the obtuse side of the lateral struts. The bend recess 408h of each bend region 406e, 408e, comprises a longitudinal length and lateral width at the lesser curvature 406g, 408g. In some variations, these lengths and widths may be configured to assist with force distribution as the stent structure is contracted into its collapsed or delivery configuration. In some examples, the bend recess may comprise a longitudinal length in the range of 50-500 microns, 50-300 microns, or 50-250 microns, and a lateral width in the range 50-500 microns, 50-350 microns, or 100-300 microns.

In some embodiments, the configuration of the lateral struts as to the orientation of the bend region and the relative configuration between the lateral strut and the longitudinal struts may vary. In the exemplary strut configuration 400 in FIG. 4A, the both bend regions are oriented toward the transition end or otherwise "pointing" to the upstream end of the valve, but in other variations, the or more bend regions may be oriented relative to the legs of the lateral strut toward the open end or downstream end of the valve.

FIG. 4B depicts another exemplary embodiment of a stent configuration 430, which comprises longitudinal struts 432, 434 and lateral struts 436, 438. Longitudinal strut segments 432a, 434a and lateral strut segments 436, 438 together form a closed perimeter of a stent opening or cell 440. Here, the legs 436a, 436b, 438a, 438b of lateral struts 436, 438 may comprise a curved or curvilinear configuration in its expanded configuration. Legs 436,438 which have a generally convex configuration at their base 436c, 436d, 438c, 438d, and a concave configuration at their bend regions 436e, 438e. In some variations, the convex/concave configuration permits a greater amount of expansion from the delivery configuration to the expanded configuration, and/or may distribute more stress and strain more along the entire length of the strut leg. The angle 444a, 444b, 446a, 446b between the longitudinal struts 432, 434 and the straight or middle portion of each leg 436i, 436j, 438i, 438j may be in the range of 25-135 degrees, 45-90 degrees or 30-60 degrees. The bend regions may also comprise a bend recess 436h, 438h with a longitudinal length and lateral width, which can be configured to adjust the force and force distribution of the stent in its delivery and expanded configurations. The one or more bend region 436e, 438e of each lateral strut 436, 438 may also optionally comprise control apertures 436k, 438k as described elsewhere herein. In FIG. 4B, the legs 436a, 436b, 438a, 438b and bend regions 436e, 438e are also oriented in the same direction, but in FIG. 4C, the legs 466a, 466b, 468a, 468b bend regions 466e, 468e are oriented in opposite directions.

Each of the strut segments or contiguous length of longitudinal or lateral struts comprises by a lateral width or dimension, a radial height or dimension, and a cross-sectional shape. The shape may be generally square, rectangular, trapezoidal or other polygonal shape, circular or ovoid shape. The lateral width or dimension of each strut segments may be configured to provide different levels of radial force, with larger widths providing greater force, and smaller widths providing less force. In variations wherein the stent structure is formed from laser cutting of a tubular base structure, the cross-sectional shape of the strut segment relative to its elongate length may comprise a segmented annular shape, as depicted in FIGS. 2A to 3B. In the specific exemplary embodiment in FIGS. 2A and 2B, struts 200a and 200b represent struts from the outer and inner wall of a stent structures, respectively. The inner wall strut 200b comprises the segmented annular shape, with an outer convex curvature 202b, farthest from the longitudinal axis of the stent structure, that is also its greater or longer curvature, and an inner concave curvature 204b, closer to the longitudinal axis of the stent structure, that is also its lesser or shorter curvature, with lateral surfaces 206b, 208b that are generally linear in cross-section but with an angular axes 210b, 212b that are generally orthogonal to the longitudinal axis of the stent structure. The outer wall strut 200a may comprise the same or similar orientation as the inner wall strut 200b initially, but in embodiment where the outer wall is formed by eversion, the outer wall struts 200a will have an everted orientation, such that its outer curvature 202a, relative to the longitudinal axis of the stent structure, is concave and also its lesser curvature, while its inner curvature 204a that is closer to the longitudinal axis of the stent structure is convex and its greater curvature is concave. The lateral surfaces 206a and 208b have angular orientations that are skewed relative to the longitudinal axis of the stent structure, e.g. the angular axes 210a, 210b of lateral surfaces 206a, 208a do not intersect the longitudinal axis of the stent structure. These configurations are also notable in that they are located on different regions of the same longitudinal strut of a unibody folded stent structure that is formed by eversion. The corresponding transition wall strut, in its expanded state, would have a similar configuration as the outer wall strut 200a in a unibody folded stent structure that is formed by eversion.

Figure 2A:
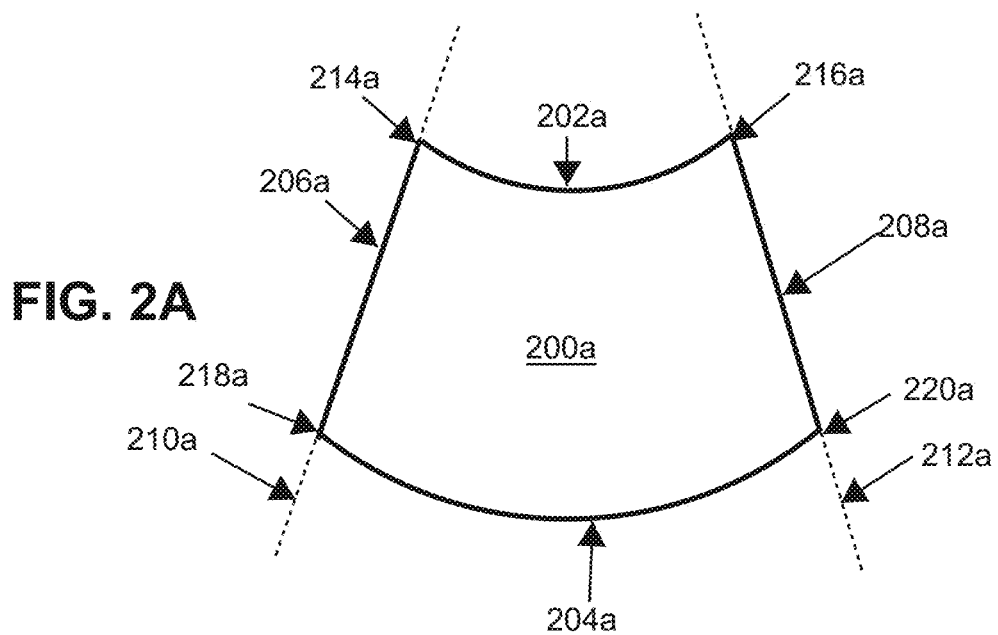
FIGS. 2A and 2B schematically depict cross-sectional configurations of struts in the outer and inner walls of an exemplary folded stent structure.
Figure 2B:
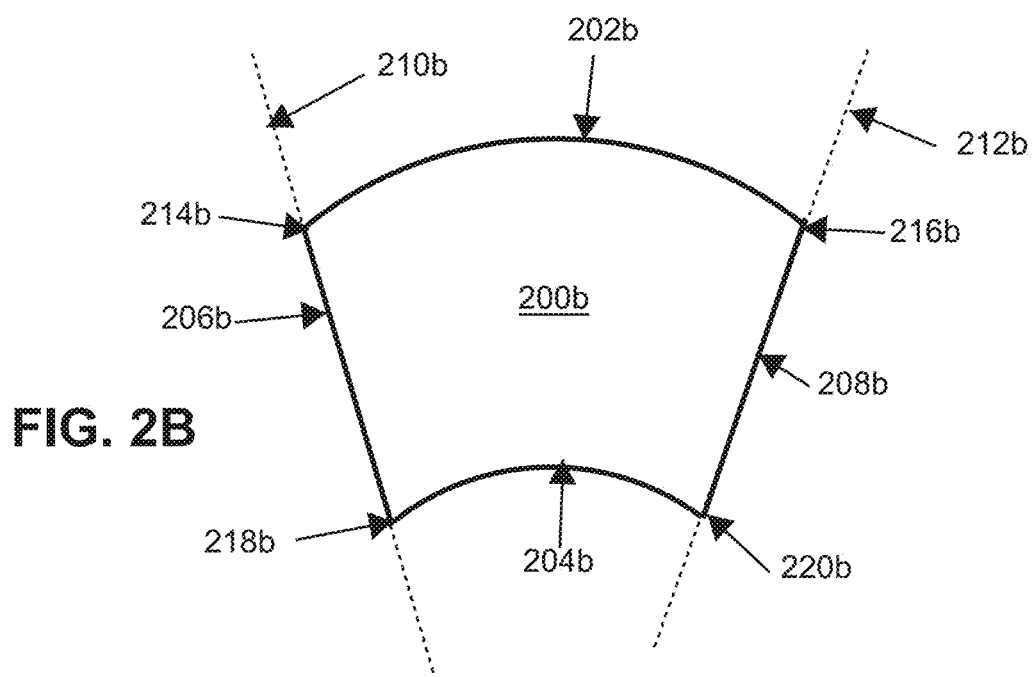
Figure 3A:
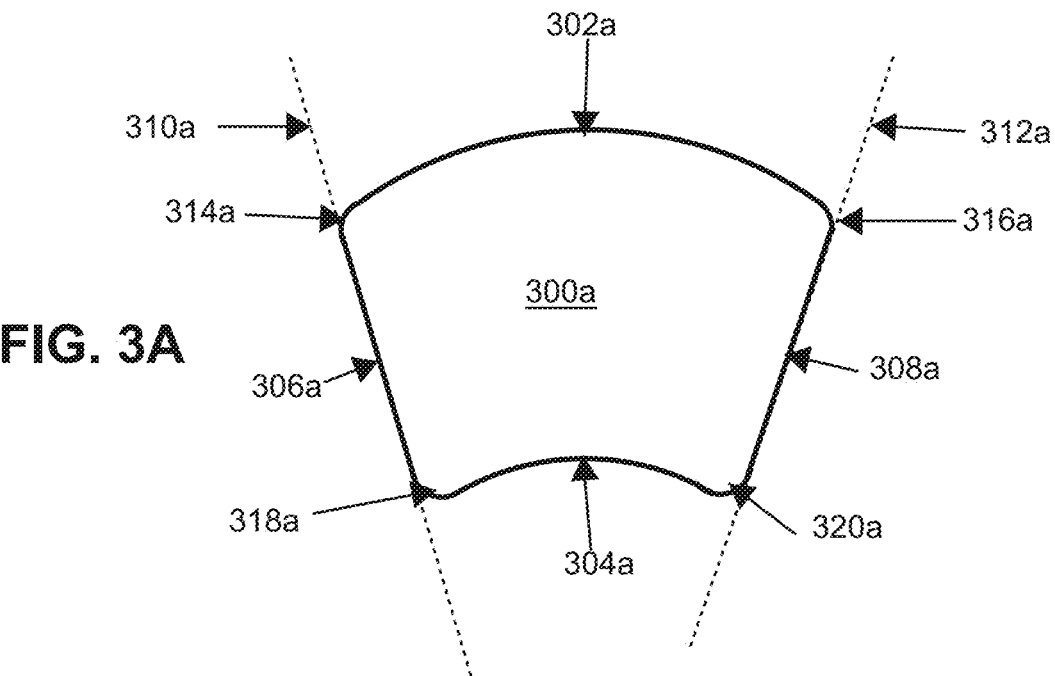
FIGS. 3A and 3B schematically depict cross-sectional configurations of struts in the outer and inner walls of another exemplary folded stent structure.
Figure 3B:
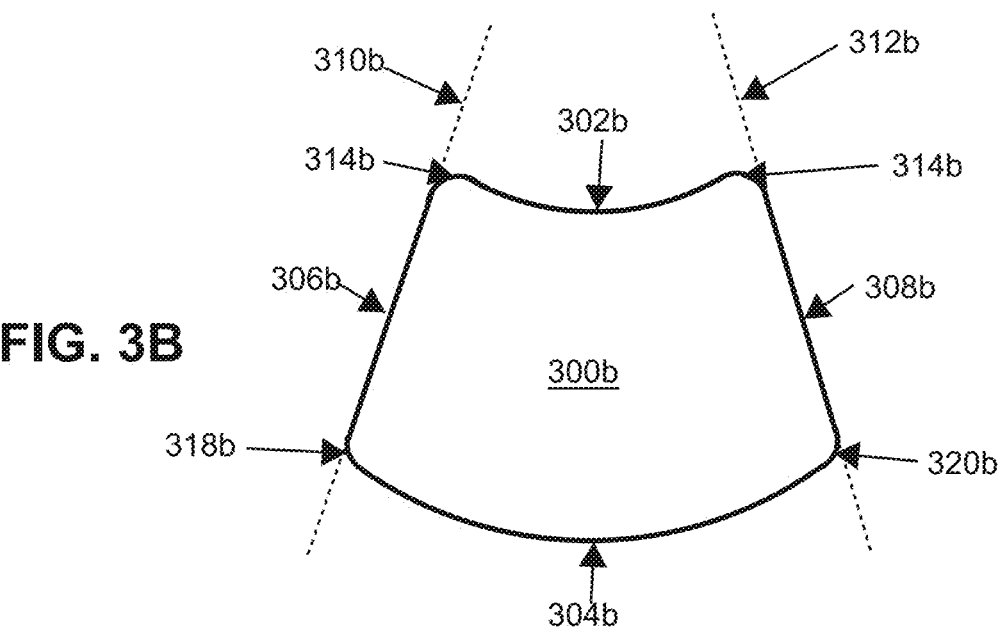

FIGS. 3A and 3B depict another embodiment of folded stent structure with a set of configurations of the struts in the outer and inner walls resulting from inversion of a laser cut tube to form the inner lumen and wall, rather than the eversion configuration depicted in FIGS. 2A and 2B. In FIGS. 3A and 3B, struts 300a and 300b represent struts from the outer and inner wall of a stent structures, respectively. The outer wall strut 300a comprises the segmented annular shape, with an outer convex curvature 302a, farthest from the longitudinal axis of the stent structure, that is also its greater or longer curvature, and an inner concave curvature 304a, closer to the longitudinal axis of the stent structure, that is also its lesser or shorter curvature. Lateral surfaces 306a, 308a are generally linear in cross-section but with an angular axes 310a, 312a that are generally skewed or non-intersecting to the longitudinal axis of the stent structure. The inner wall strut 300b may comprise the same or similar orientation as the outer wall strut 300a initially, but in embodiment where the inner wall is formed by inversion, the inner wall struts 300b will have an inverted orientation, such that its outer curvature 302b, relative to the longitudinal axis of the stent structure, is concave and also its lesser curvature, while its inner curvature 304b that is closer to the longitudinal axis of the stent structure is convex and also its greater curvature is concave. The lateral surfaces 306b and 308b have angular orientations that are skewed or non-intersecting relative to the longitudinal axis of the stent structure. Like the everted configuration of the folded stent structure, these outer and inner wall configurations are located on different regions of the same longitudinal strut of a unibody folded stent structure that is formed by inversion. The corresponding transition wall strut, in its expanded state, would have a similar configuration as the outer wall strut 200a in a unibody folded stent structure that is formed by inversion. In some variations, the resulting radial force in the outer wall of the stent structure may be greater with an inverted stent structure, as compared to an everted stent structure, as the everting or inverting process may weaken or adversely affect that portion of the stent structure, compared to the portion that does not undergo eversion or inversion.

The edges of the polygonal shaped struts may be rounded, smooth or sharp. In FIGS. 2A and 2B, the corners 214a-220b comprise well defined angular edges, while FIGS. 3A and 3B, the corner edges 314a-320b comprises rounded corners. The rounded corners and edges may be formed using mechanical polishing, chemical electropolishing, or multi-step combinations thereof, e.g. mechanical polishing, followed by chemical polishing or electropolishing. In some variations, the polishing may be performed before any inversion or eversion of the laser cut tubing. The dimensions and/or shape of the strut segments or struts may be uniform or may vary along its length. The radial thickness and/or the circumferential width of the struts may be in the range of 300-500 microns, 360-460 microns, or 400-500 microns. The strut thickness and/or width mayor may not be uniform along the length of a strut segment. As noted previously, in some examples, relatively larger widths may be provided at the base of a circumferential strut segment, and relatively smaller widths may be provided about the middle bend regions.

The spacing between adjacent longitudinal or circumferential struts may be equal throughout the folded stent structure or may be different along the folded stent structure. For longitudinal struts, the number of struts may vary depending on the desired flexibility or radial expansion force desired for the stent structure, or based on the desired strut segment width to achieve the desired radial expansion force or flexibility. For circumferential struts, a relatively larger spacing may be provided in areas were greater radial expansion and/or reduced expansion force is desired, and small spacing in areas of reduced radial expansion and/or greater expansion force is desired.

The various stent structures described herein may comprise one or more of the following characteristics 1) a net longitudinal stent length (i.e. the maximum distance spanned by the stent along the longitudinal axis) in the range of 15-60 mm, 20-40 mm, or 25 to 35 mm;
2) a folded longitudinal stent length (e.g. the longitudinal length of the end to end contiguous longitudinal strut if completely straightened out) in the range of 40-100 mm; 50-90 mm; 60-80 mm;
3) a maximum stent diameter or transverse dimension in the expanded configuration in the range of 20-80 mm, 30-60 mm, or 45-55 mm;
4) a maximum outer end diameter or transverse dimension in the expanded configuration in the range of 25-75 mm, 35-65 mm, or 48-58 mm;
5) a maximum transition end diameter or maximum transition end transverse dimension in the expanded configuration in the range of 20-80 mm, 25-55 mm, or 40-50 mm, and is optionally less than the maximum outer end or maximum stent diameter or transverse dimension by 0-20 mm, 1-15 mm, 2-10 mm, 2-8 mm, or 2-5 mm;
6) an inner lumen length in the range of 10-50 mm, 15-40 mm, or 20-26 mm;
7) an inner lumen diameter or maximum cross-sectional dimension in the range of 10-40 mm, 15-35 mm, or 26-31 mm;
8) an inner upper radius of curvature $R_1$ in the range of 1-10 mm, 2-8 mm or 3-5 mm;
9) an inner upper bend angle in the range of 0-180 degrees, 60-135 degrees, or 75 to 90 degrees, or 83 degrees;
10) a transition wall external angle relative to the longitudinal axis of the stent structure in the range of 0-180 degrees, 45-100 degrees, 75-90 degrees, or 90 degrees;
11) a transitional wall radial width in the range of 5-30 mm, 5-20 mm, or 5-10 mm;
12) an outer upper radius of curvature $R_2$ in the range of 0.5-6 mm, 1.5 to 5 mm, or 2.5 to 4 mm;
13) an outer upper bend angle $A_2$ in the range of 45-270 degrees, 90-235 degrees, 135-200 degrees, or 160 to 200 degrees;
14) an outer wall longitudinal length in the range of 10-40 mm, 20-35 mm, or 25-30 mm;
15) an outer wall curvilinear length in the range of 10-50 mm, 20-50 mm, or 30-40 mm;
16) an outer wall longitudinal strut length from the outer end to the transition wall in the range of 12-50 mm, 20-40 mm, or 25-35 mm;
17) an outer wall middle region radius of curvature in the range of 1-15 mm, 3-12 mm, 4-8 mm, or 3-6 mm;
18) an outer wall middle region bend angle in the range of 10-180 degrees, 30-160 degrees, 60-160 degrees, or 80-140 degrees;
19) an outer wall open end region or lower region radius of curvature $R_4$ in the range of 5-100 mm, 5-40 mm, mm, or 10-20 mm;
20) an outer wall open end region or lower region bend angle $A_4$ in the range of 1-90 degrees, 10-90 degrees, 20-80 degrees, or 30-70 degrees;
21) a maximum radial difference between the smallest radius and largest radius in the same radial plane of the outer wall of the stent structure is in the range of about 6-15 mm, 8-12 mm, 9-11 mm, or about 10 mm;
22) a first end/atrial/upper region maximum radius of the outer wall in the range of 20-30 mm, 22-28 mm, or 24-27 mm;
23) a middle region minimum radius of the outer wall in the range of 10-30 mm, 12-25 mm, or 15-20 mm;
24) a second end/ventricular/lower region maximum radius of the outer wall in the range of 20-35 mm, 25-30 mm, or 26-29 mm;
25) a longitudinal length to diameter ratio in the range of 0.40 or 1.0, 0.45 to 0.80, or 0.50 to 0.60;
26) a number of longitudinal struts that is divisible by 3, e.g. selected from a group consisting of one or more of 3, 6, 9, 12, 15 longitudinal struts;
27) a ratio between the radial distance between the barb tip and the longitudinal axis of the stent structure, and the radial distance between an adjacent longitudinal strut or outer wall segment (excluding the barb) and the longitudinal axis of the stent structure, in the range of 1.1 to 1.5, 1.05 to 1.30, 1.05 to 1.20, or 1.05 to 1.15; and/or
28) an inner opening position relative to the outer opening position along the longitudinal axis that is positive (i.e. protrudes from the outer opening), neutral (i.e. flush with the outer opening), negative (i.e. recessed from the outer opening), and/or in the range of −4 to −12 mm, −5 to −10 mm, −6 to −9 mm, +1 to +8 mm, +2 to +6 mm, +3 to +5 mm, −3 to +3 mm; +0 to +3 mm, −12 to +5 mm, −6 to +6 mm, or −7 mm to +4 mm.

The scope of stent structures described herein need not be limited so as to require a selection of each characteristic recited above, and single characteristics or a subset of characteristics are also contemplated. For example, in some variations, the stent structure, which may or may not be provided with the valve and/or skirt material, may be:

1) a folded unibody stent structure with an everted outer wall strut configuration or an inverted inner wall strut configuration;
2) a folded unibody stent structure and wherein the number of longitudinal struts divisible by 3; with a non-foreshortening inner lumen, and optionally a foreshortening outer wall, with a radial strut thickness in the range of 400-450 microns and a longitudinal length to diameter ratio in the range of 0.50 to 0.60;
3) a folded unibody stent structure comprising an upper inner radius of curvature that is smaller than the upper outer radius of curvature, an inner lumen that extends from the outer opening of the outer wall by 0 to 3 mm, and a barb to outer wall radius ratio in the range of 1.1 to 1.2; or
4) a folded double-wall unibody stent structure 12 longitudinal struts and 3-5 circumferential struts in the inner lumen, 1-2 circumferential strut in the transition wall and 3-5 circumferential struts in the outer wall.

Figure 1C:
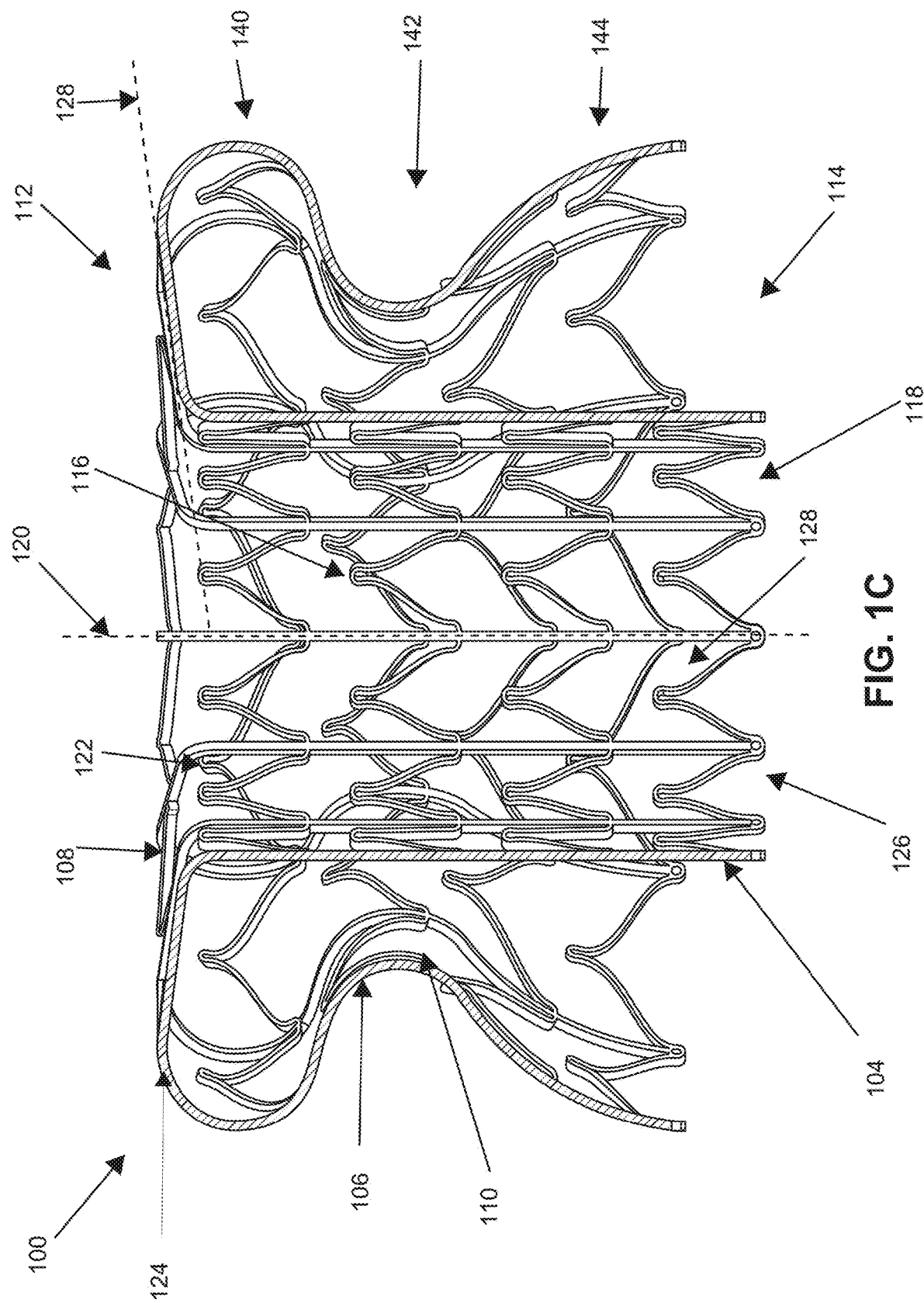
FIG. 1C is a partial cross-sectional view of the heart valve stent of FIG. 1A with a portion of the outer wall omitted.
Figure 1D:
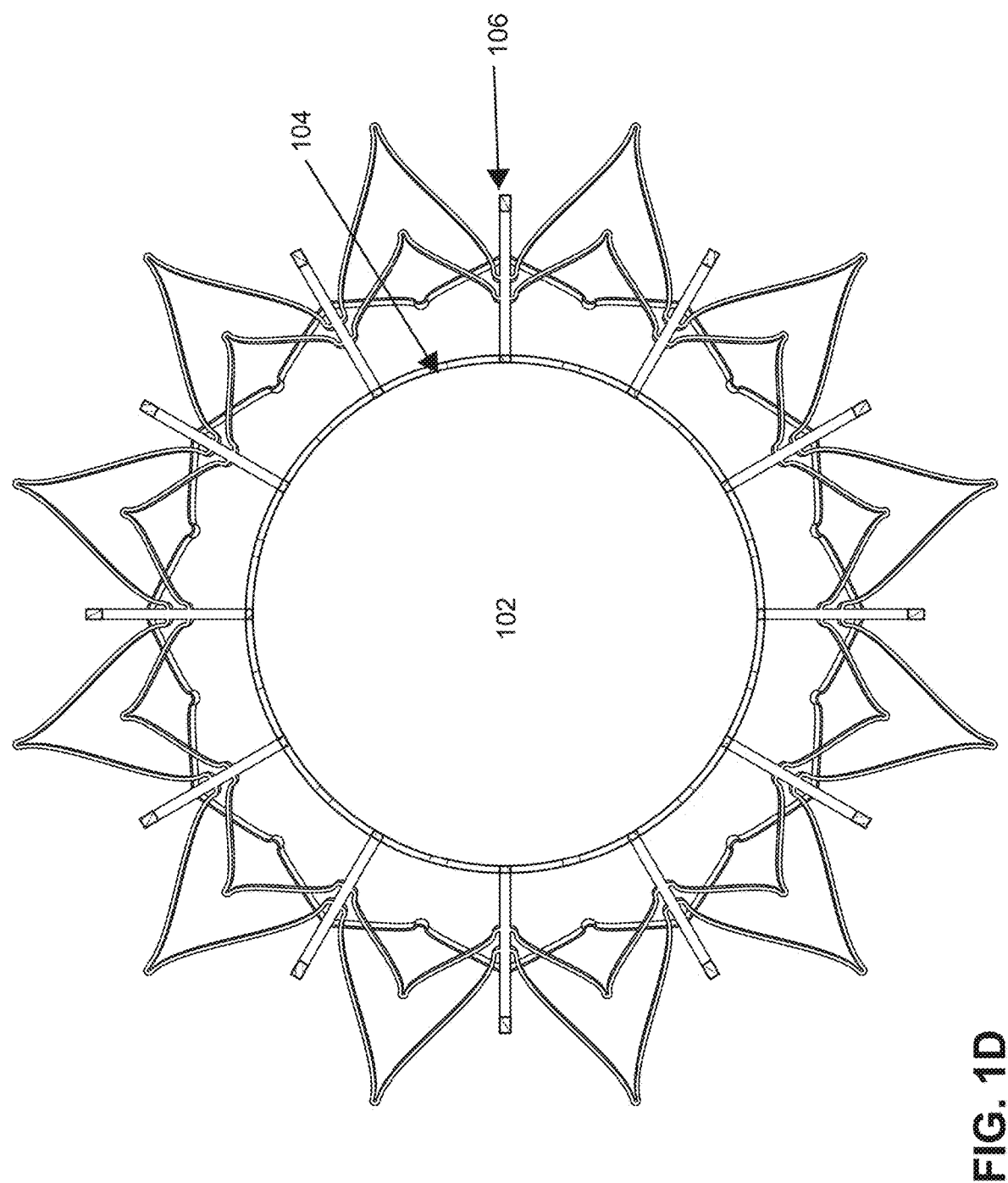
FIG. 1D is a schematic cross-sectional view of FIG. 1B.
Figure 1E:
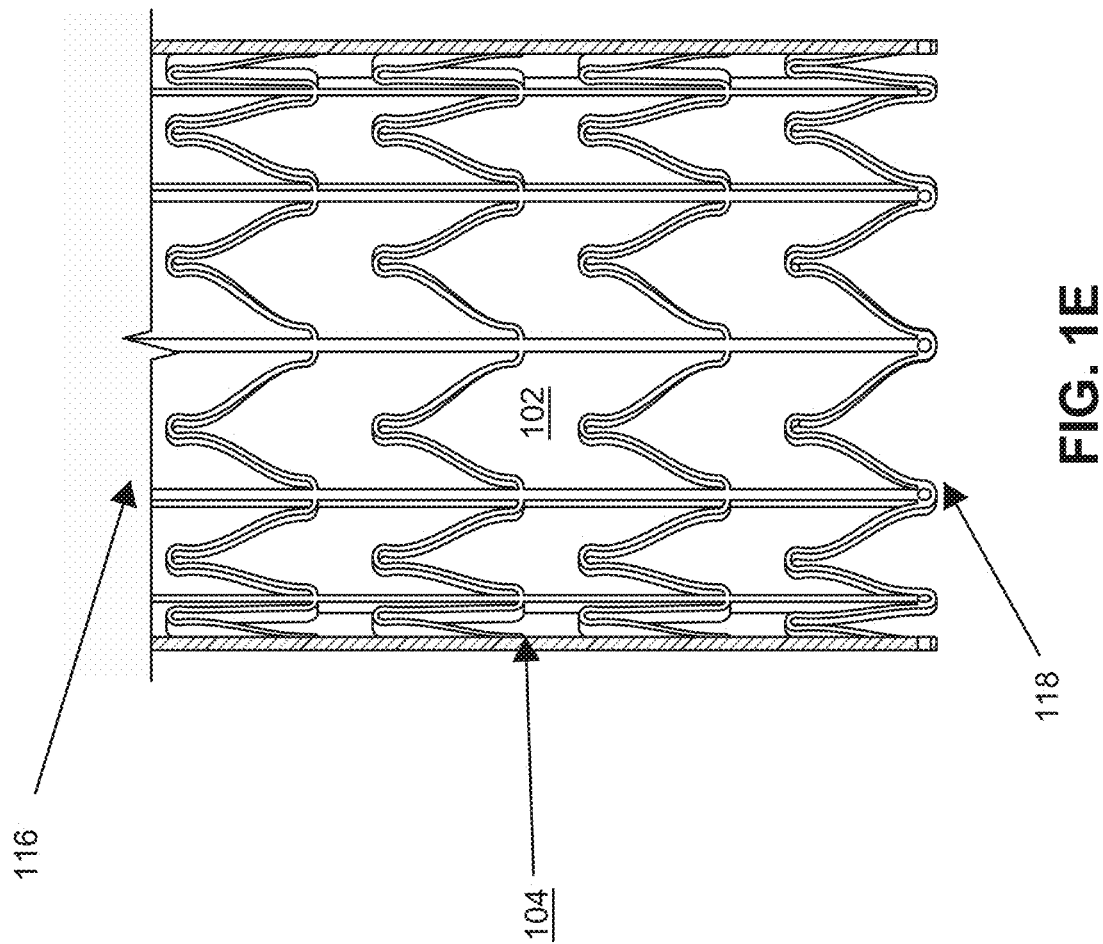
FIG. 1E is a schematic cross-sectional view of the inner wall of the heart valve stent, without the outer wall.
Figure 1F:
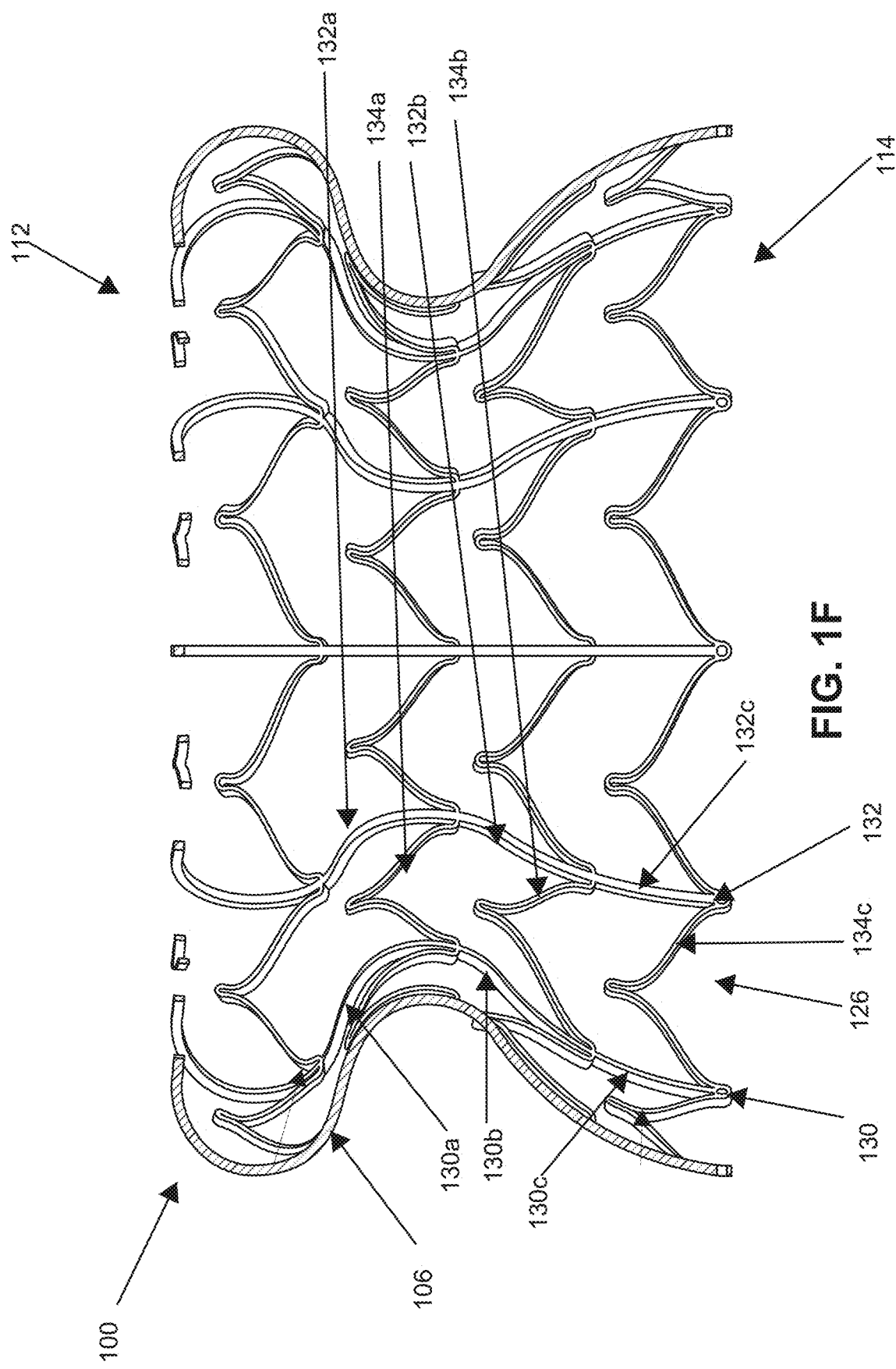
FIG. 1F is a schematic cross-sectional view of the outer wall of the heart valve stent, without the inner wall.
Figure 1G:
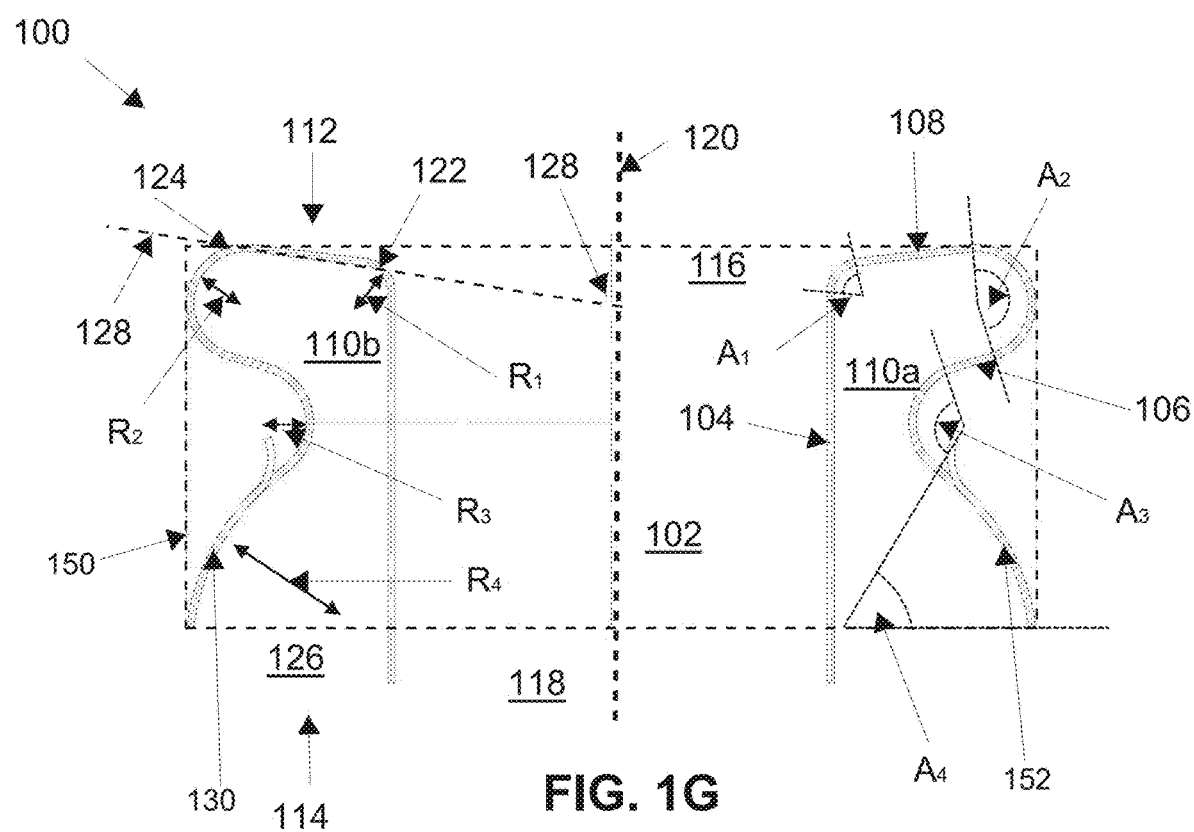
FIG. 1G is a schematic component view of two longitudinal struts from FIG. 1A.

In the embodiment depicted in FIGS. 1A to 1G, the stent structure 100 comprises a plurality of end-to-end longitudinal struts and a plurality of circumferential lateral struts, each in turn comprising a contiguous set of contiguous longitudinal or lateral strut segments, respectively. In the particular example of stent structure 100, twelve equally spaced apart end-to-end longitudinal struts are provided, and nine sets of complete circumferential struts along the folded stent structure 100. Four sets of closely spaced circumferential struts are provided along the inner wall, with relatively straight or minimally curved legs and with their middle bends oriented to point toward the upper or closed end of the stent structure. The transition wall 108 comprises one set of circumferential struts with a relatively increased base curvature in each leg and a relatively reduced curvature about the middle bend oriented to point radially outward toward the outer wall 106. The outer wall 106 comprises four sets of circumferential struts, with their middle bends oriented toward the closed end of the stent structure 100, except for the set of circumferential struts closest to the opening of the outer wall 106, which may be oriented toward the open end of the stent structure 100. The orientation of the legs and middle bends in the third set of circumferential struts also deviates radially outward relative to the adjacent longitudinal struts to provide barb-like or force concentration structures resist displacement of the strut structure relative to the native valve tissue. Typically, these radially outward displaced circumferential struts may be provided at one or more circumferential struts that are closest to the portion of the outer wall between the narrowest diameter and the downstream or open end of the stent structure, and oriented toward the narrowest diameter or inlet/upstream end of the stent structure, as shown in FIGS. 1A and 1C.

As noted previously, control apertures are also provided at the outer end of, or at the junction of the longitudinal struts and the circumferential strut at the outer end of the stent structure 100, and at the inner end of, or at the junction of the longitudinal strut and the circumferential strut at the inner end of the stent structure, at the inner lumen. Control apertures are also provided at the middle bends of the two circumferential struts closest to the outer end of the stent structure 100.

For stent structure 100, the net longitudinal stent length may be 25 to 35 mm, the folded longitudinal stent length may be 60-90 mm, the maximum stent diameter or transverse dimension in the expanded configuration may be 45-55 mm, the maximum outer end diameter or transverse dimension in the expanded configuration may be 45-55 mm, the maximum transition end diameter or transverse dimension in the expanded configuration may be 40-50 mm, and may be less than the maximum outer end or maximum stent diameter or transverse dimension by 1-5 mm, the inner lumen length may be 20-25 mm, the inner lumen diameter or maximum cross-sectional dimension is 20-30 mm, the inner upper radius of curvature may be 3-5 mm, the inner upper bend angle may be 90 to 105 degrees, the transition wall external angle relative to the longitudinal axis of the stent structure may be 75-90 degrees, the transitional wall radial width may be 15-20 mm, the outer upper radius of curvature in the range may be 1 to 4 mm, the outer upper bend angle may be 160 to 200 degrees, the outer wall longitudinal length may be 20-25 mm, the outer wall curvilinear length may be 25-40 mm, the outer wall longitudinal strut length from the outer end to the transition wall may be 25-35 mm, the outer wall middle region radius of curvature may be 3-6 mm, the outer wall middle region bend angle may be 60-120 degrees, the outer wall open end region or lower region radius of curvature may be 10-50 mm, 10-30 mm, or 10-20 mm, the outer wall open end region or lower region bend angle may be 20-135 degrees, 30-90 degrees, or 50-70 degrees, the maximum radial difference between the smallest radius and largest radius in the same radial plane of the stent structure may be 9-11 mm, and/or the inner opening position relative to the outer opening position along the longitudinal axis that is negative may be −6 to −9 mm.

In FIGS. 1A to 1F, the stent structure 100 also comprises twelve contiguous longitudinal struts, and nine circumferential struts as with stent structure 100. Stent structure 100 comprises four circumferential struts along the inner lumen 102, but in other variations may have two, three, five or six circumferential struts in the inner lumen. While the orientations of the circumferential struts in the inner wall 104 are also pointed toward the closed end of the stent structure 100, and the circumferential strut of the transition wall 108 are oriented radially outward, in some variations, one or more circumferential struts that are oriented radially inward and/or toward the open end of the stent structure, e.g. the circumferential strut closest to the open end of the outer wall. Other optional variations may include a transition wall with has an orthogonal orientation relative to its longitudinal axis, while the transition wall 108 of stent structure 100 is slight or substantially angled. It is hypothesized that an inwardly angle transition wall may reduce turbulence or non-laminar flow into the opening of the inner lumen, or peak axial forces that may dislodge the stent structure from the target location during atrial contraction.

In several of the embodiments described herein, the upper end or transition end of the stent structure is configured to be used as the upstream end of the replacement valve, with blood flow received in the transition end of the inner lumen and to pass through the valve structure attached to the inner lumen. The valve structure may be any of a variety of valve structures, including a flap valve, ball-in-cage valve, or a leaflet valve. The leaflet valve material may comprise an autologous, homologous or heterologous or artificial material, e.g. a natural material or anatomical structure, such as porcine, bovine or equine pericardial tissue or valve, or biomaterials derived from the patient's own cells, and may be fixated with any of a variety of chemicals, such as glutaraldehyde, to decrease the antigenicity of the valve and/or to alter the physiological and/or mechanical properties of the valve materials. Where a leaflet valve is provided, the leaflet valve may be a bi-leaflet or tri-leaflet valve structure. The commissures of the valve may be attached or sutured to the longitudinal and/or circumferential struts of the inner lumen, e.g. every fourth longitudinal strut of the stent structures 100 provided with a tri-leaflet valve.

The replacement valve may further comprise one or more skirt materials to one or more regions of the stent structure. The skirt materials may comprise solid, tight weave, or loose knit woven sheet of autologous, homologous or heterologous or artificial material that may be the same or different from the leaflet material of the valve. The skirt material may comprise polytetrafluoroethylene (PTFE), polyester or polyethylene terephthalate (PET) material. In variations comprising open pore materials, the average pore size may be in the size range of about 0.035 mm to 0.16 mm, or 0.05 mm to 0.10 mm, or 0.07 mm to 0.09 mm. The open pore materials may provide greater elasticity or flexibility in regions of the stent structure that undergo greater configuration change. Other regions of the stent may be provided with a solid sheet materials, lacking pores, where elasticity or flexibility are not needed. The skirt material may comprise a single layer or a multi-layer structure, and comprise one or more coatings to modulate thrombus formation, tissue ingrowth, and/or lubricity.

Figure 5A:
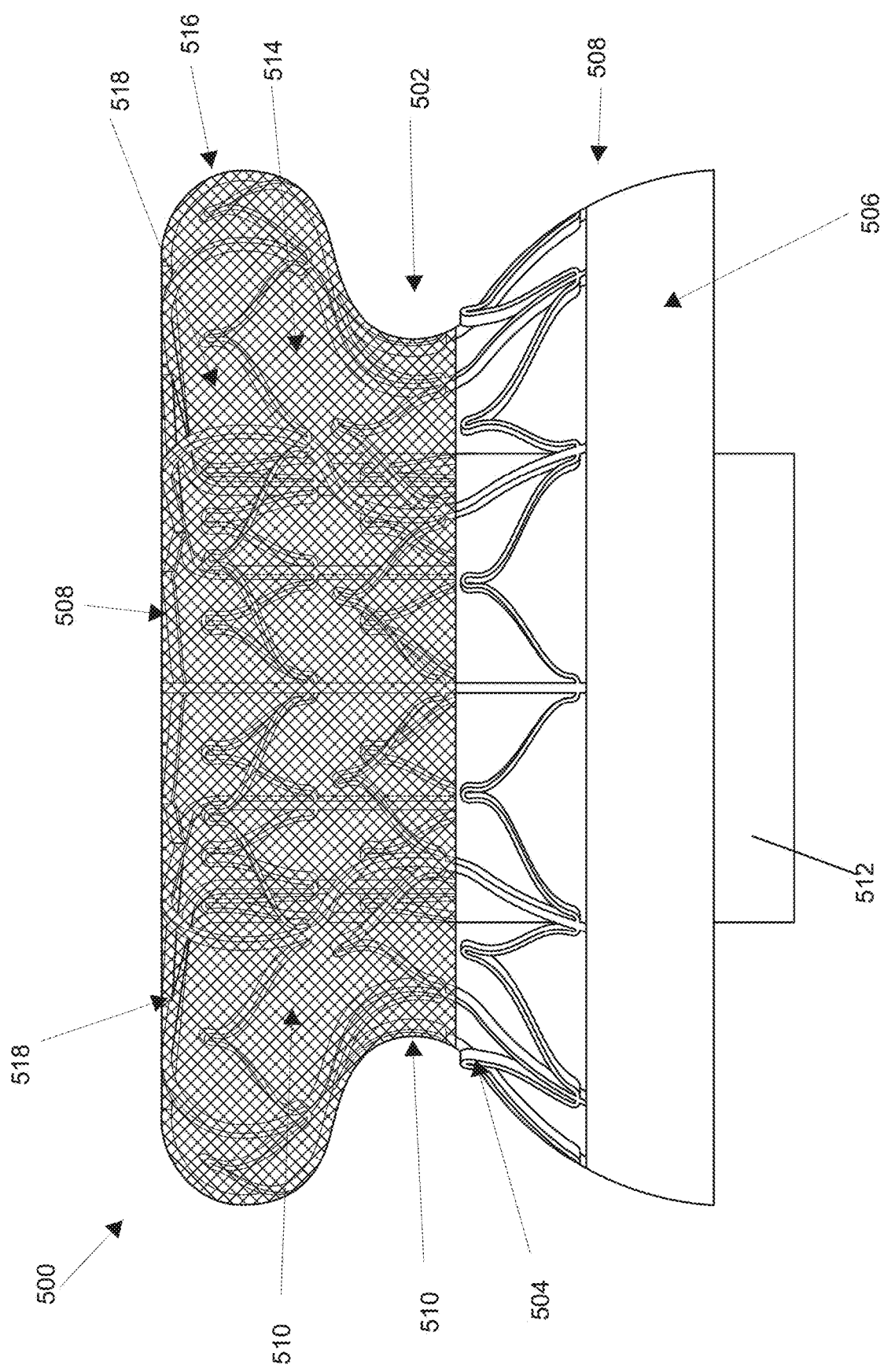
FIG. 5A is a schematic side elevation view of another embodiment of a heart valve stent with the leaflet valve and skirt attached.
Figure 5B:
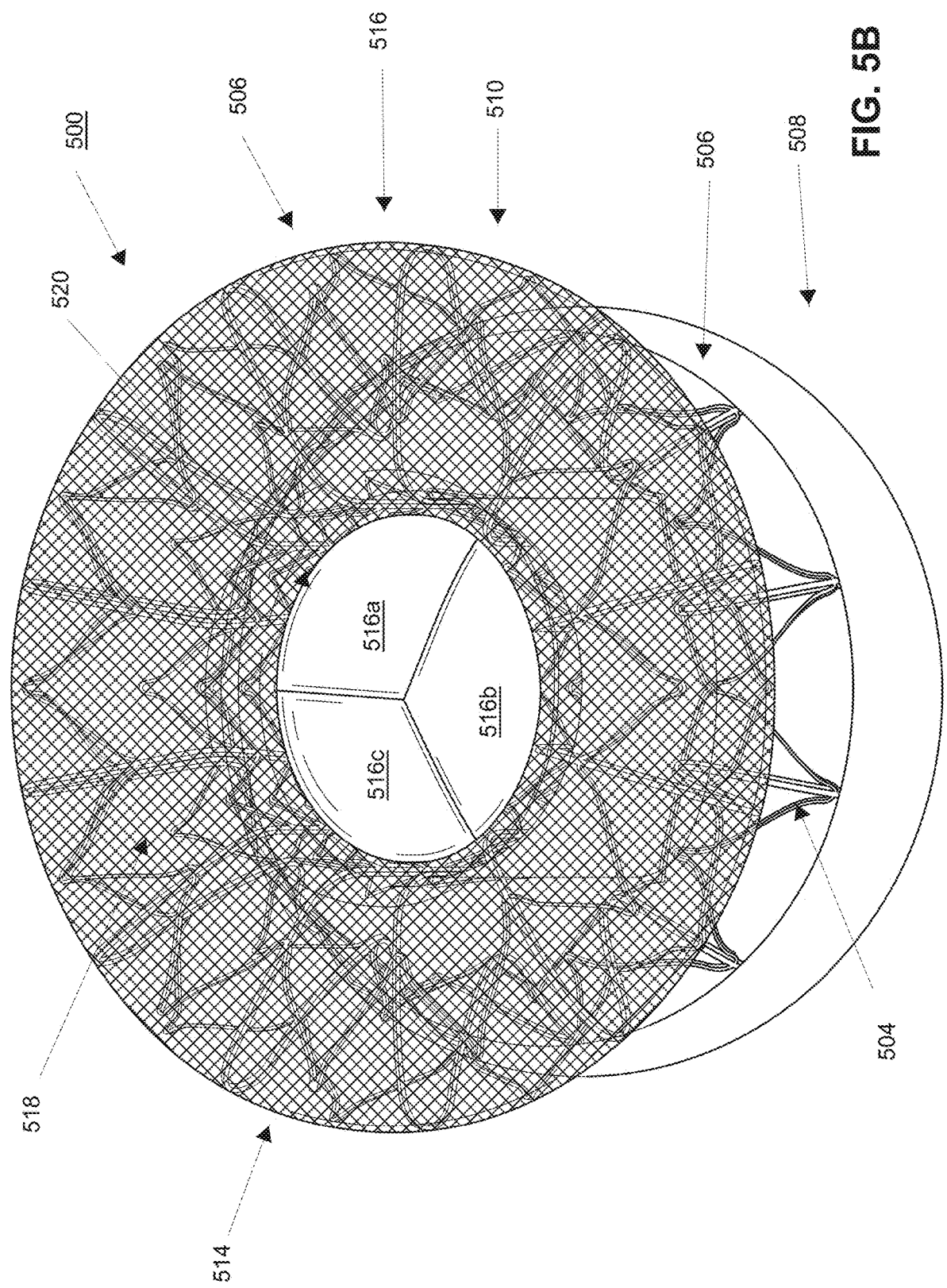
FIGS. 5B and 5C are schematic bottom and top perspective view of the heart valve stent in FIG. 5A.
Figure 5C:
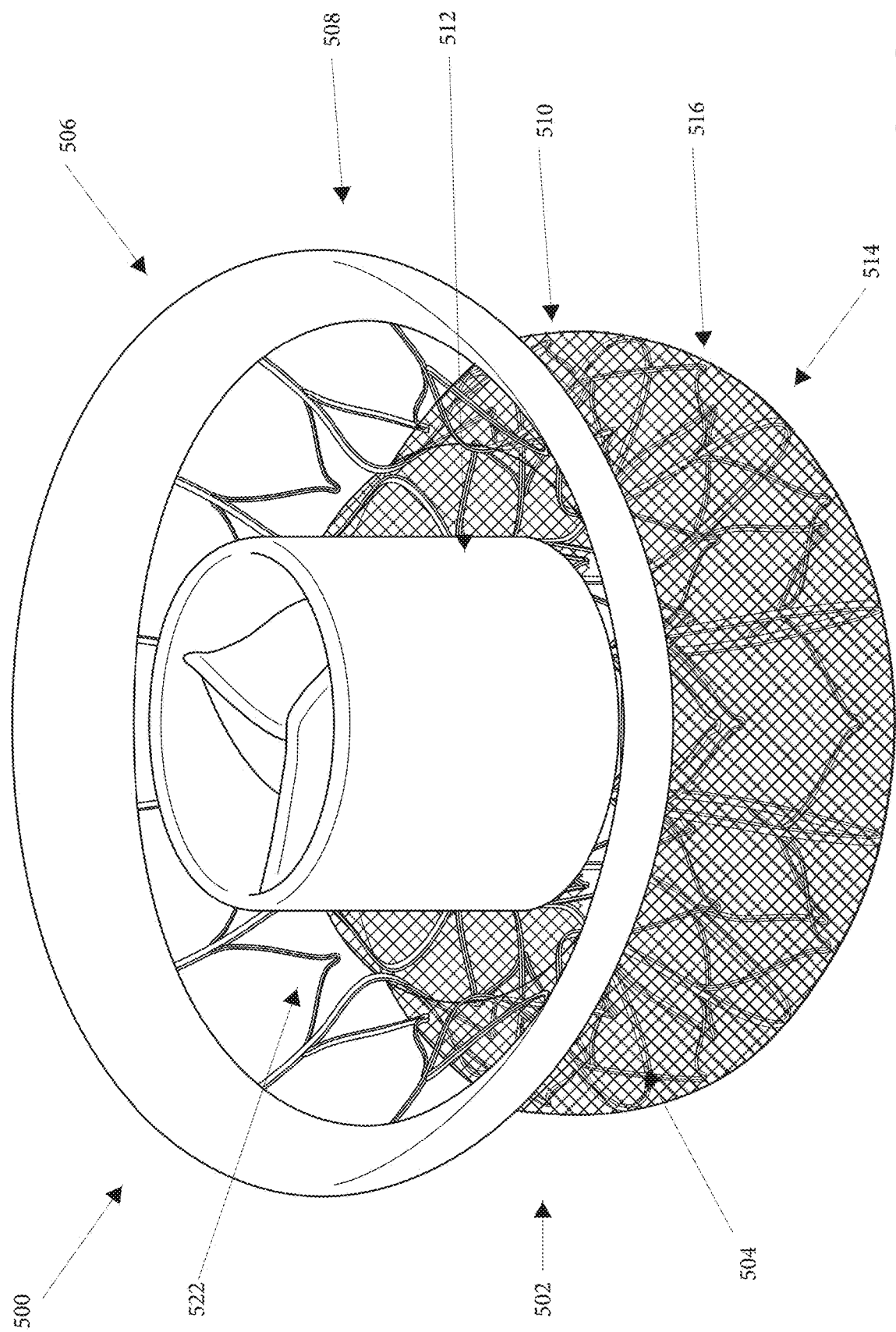
Figure 5D:
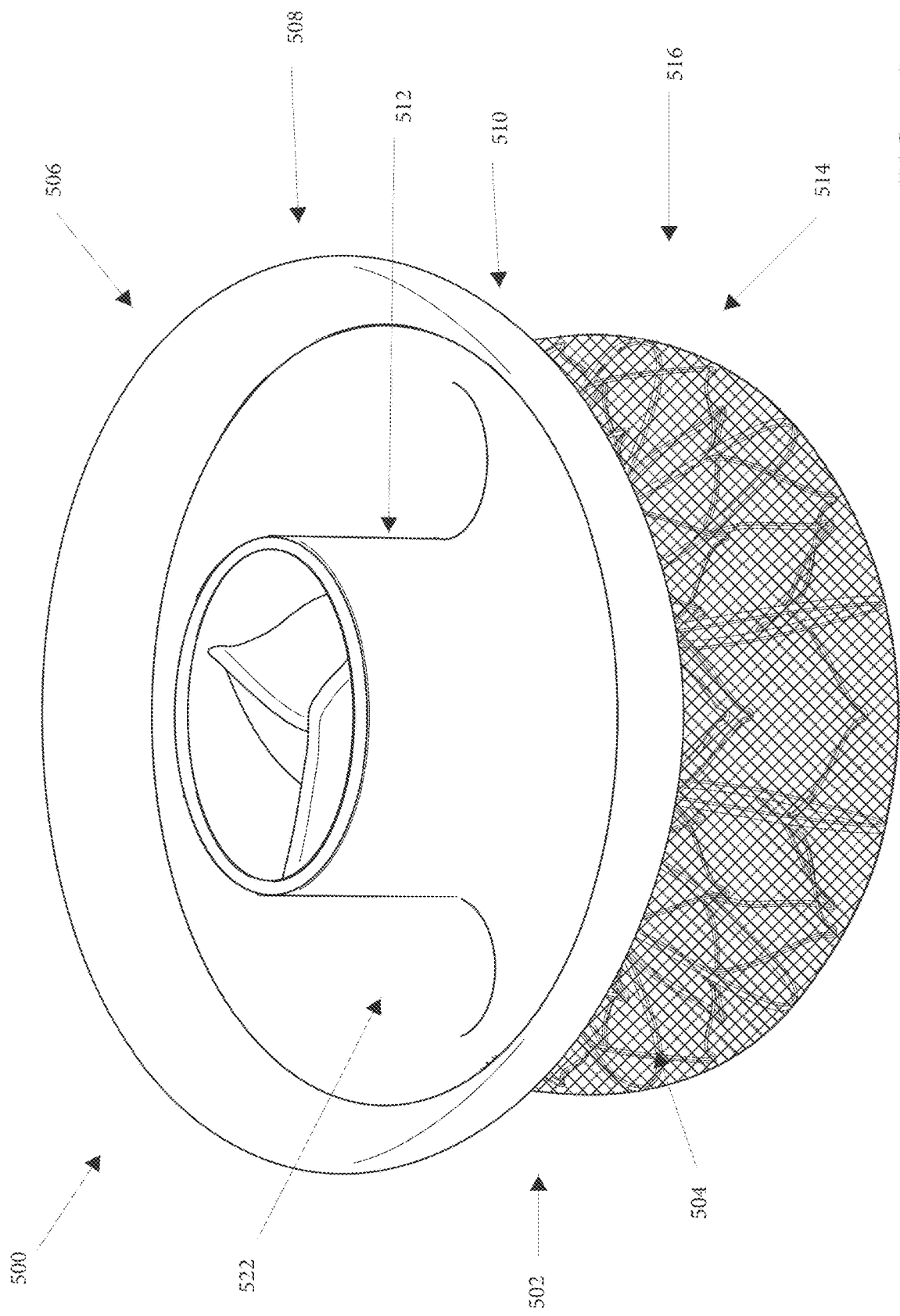
FIG. 5D is a schematic top perspective view of a variant of the cuff structure in FIG. 5C.
Figure 6A:
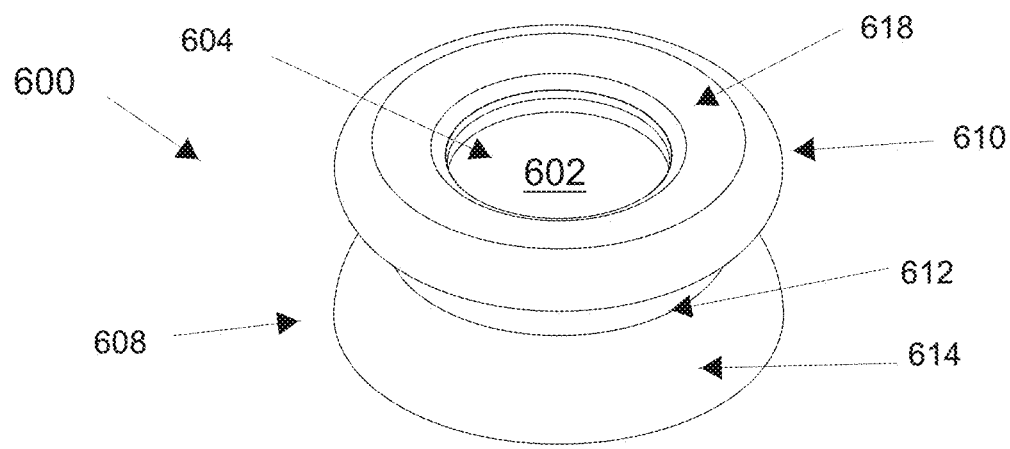
FIGS. 6A to 6C are top perspective, top plan and side elevation views of a skirt structure for use with a heart valve stent.
Figure 6B:
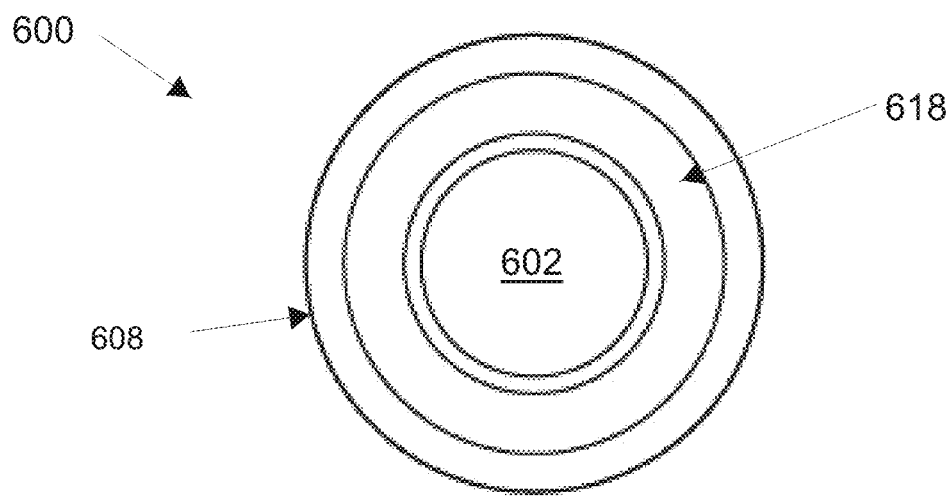
Figure 6C:
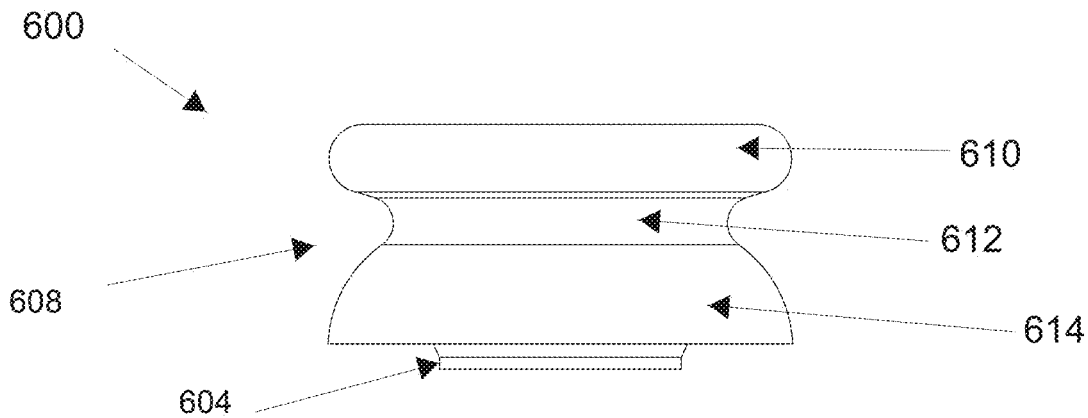
Figure 6D:
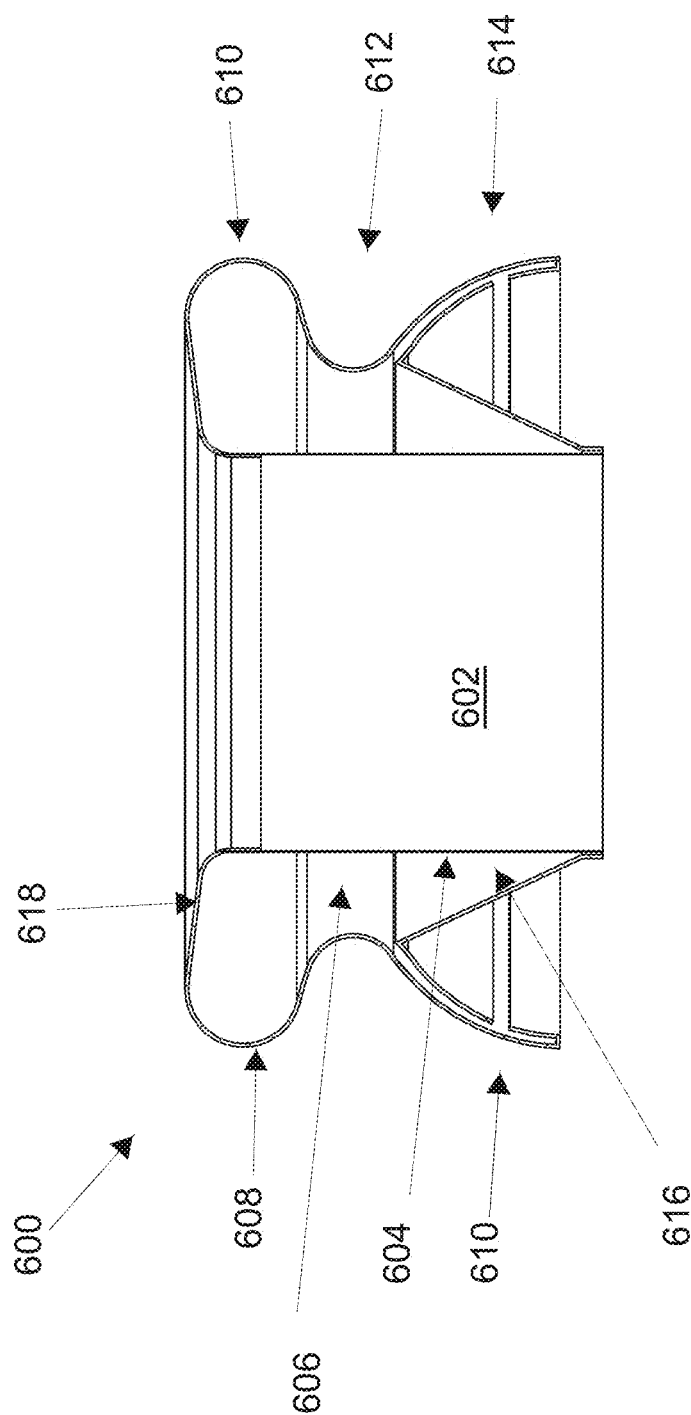
FIG. 6D is a cross-sectional view of the skits structures in FIGS. 6A to 6C.

FIGS. 5A to 5C depict one example of a replacement valve 500 with a skirt 502 comprising two different materials attached to the stent structure 504. In this particular embodiment, a solid or tight weave material is provided as a cuff structure 506 around the outer and inner surfaces of the downstream or lower region 508 of the outer wall 510. The same or a different cuff structure of the solid or tight weave material is provided on the outer surface of the inner wall 512. FIG. 5C depicts a variant with separate material for the inner wall 512, and FIG. 5D depicts another variant with the same cuff structure spanning the annular cavity 522 and covering the outer surface of the inner wall 512. A porous knit material is used for another cuff structure 514 around the upper region 516 of the outer wall 510, the transition wall 518 and to the upstream opening 520 of the inner wall 512 of the stent structure 504. An artificial or animal-derived material may be used to form the valve pockets and valve leaflets 516a-c located in the inner lumen 512. In addition to provide elasticity to expand with the expansion of the stent structure, the porous knit material may also provide for cellular migration and tissue ingrowth into the replacement valve. This dual material skirt 502 permits blood that flows into the annular cavity 522 of the to pass through the porous material of cuff structure 514, but the porous material may be provided with a porosity that is small enough to resist the passage of thrombus that might have formed.

In another variation, depicted in FIGS. 6A to 6D, the skirt 600 comprises a tubular material. The shaped skirt 600 may provide a more consistent attachment of the skirt 600 to a stent structure with less potential problems with excess sheet material in narrower stent regions, In this particular variation, the skirt 600 comprises an internal central cavity 602 formed by an inner wall 604, and an internal annular cavity 606 between the inner wall 604 and the shaped outer wall 608. The outer wall 606 may be shaped to a complementary configuration to the outer wall of the stent structure, e.g. an expanded upstream region 610, a reduced diameter middle region 612, and an enlarged diameter downstream region 614. The skirt 600 is placed over the closed end of the stent structure so that the stent structure is located in the annular cavity 606 and where the inner wall 604 of the skirt 600 is positioned inside the inner lumen of the stent structure. In some variations, the inner wall 604 may be inverted into the inner lumen of the stent structure. A tapered annular skirt 616 may be provided to span the annular cavity 606 between the inner wall 604 and the shaped outer wall 608. The outer wall 608 of the skirt 602 may comprise a porous or knitted material that may be heat set into the expanded configuration and span the entire outer wall 606, the transition wall 618 of the skirt 602 and optionally a portion of the inner wall 606, where it is sewn, adhered, and/or welded to a tubular tight weave material configured to line the inner lumen of the stent structure. The tapered annular skirt 616 may also be sewn, adhered welded or otherwise attached to the inner surface of the outer wall 606 and the outer surface of the inner wall 604 after the outer wall 606 and inner wall 604 are initially assembled with the stent structure. Similarly, the valve leaflet structure may be sewn, adhered welded or otherwise attached to the inner wall 604 of the skirt 600, after the inner wall 604 is inserted into the inner lumen of the stent structure.

The skirt materials may be sutured against the outer and/or inner surfaces of the inner wall, transition wall, and/or outer wall of the stent, and in some variations may be provided as a cuff or folded structure over the outer end, inner end or transition wall of the stent structure to span over the inner and outer surfaces of a stent wall, or to transition from an inner or outer surface of one wall to another wall, e.g. lining the annular cavity of the replacement valve, so as to cover the inner surface of the outer wall, the inner surface of the transition wall and the outer surface of the inner wall, for example.

Figure 7A:
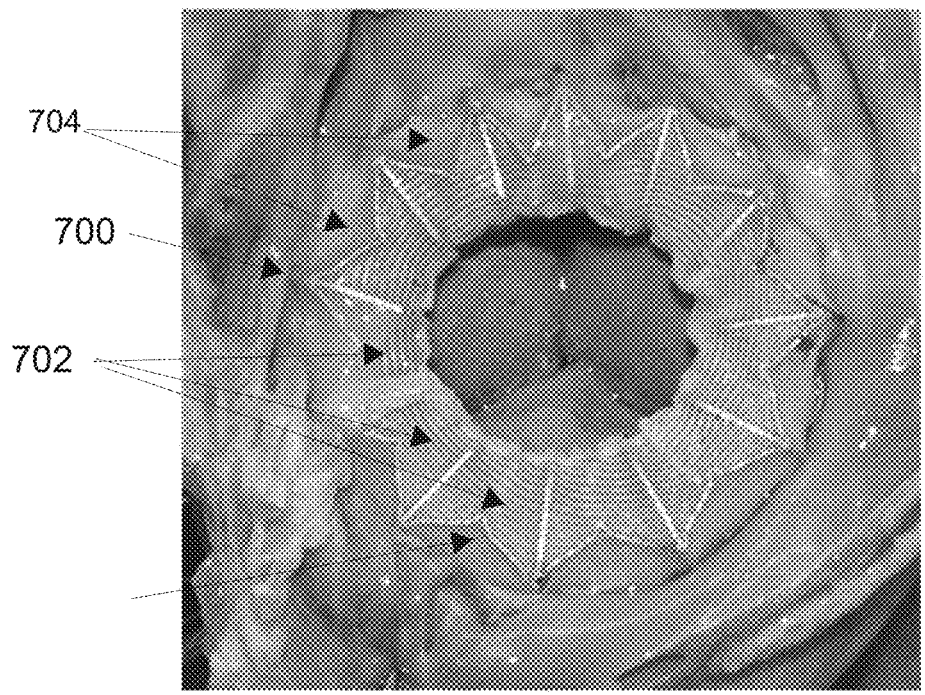
FIGS. 7A and 7B are atrial/top and ventricular/bottom views of an implanted heart valve.
Figure 7B:
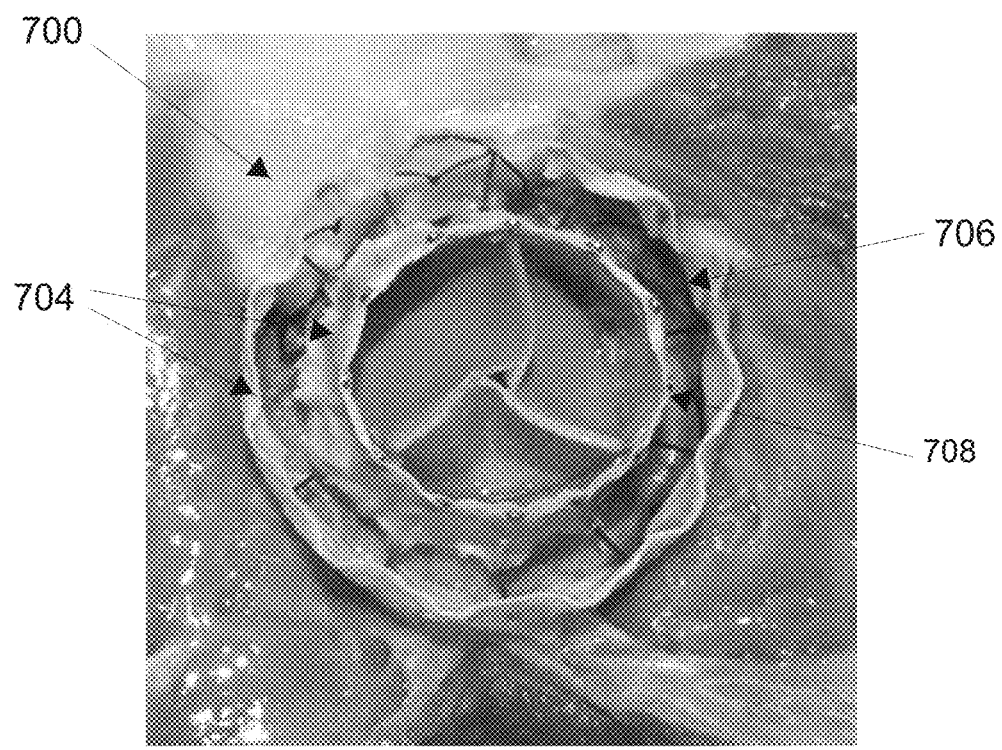

FIGS. 7A and 7B are photographs of an exemplary replacement valve 700 with a dual material skirt as described with respect to FIGS. 5A and 5B above, used in a mitral valve animal study, explanted after 30 days. On the atrial side of the valve 700 depicted in FIG. 7A, tissue or cellular ingrowth into the large pore knitted fabric 702 was found, as well as good ingrowth at the boundary or junction between the large port knitted fabric 702 and the tight weave fabric, while on the ventricular side of the valve 700, which is primarily covered by a small pore tight weave fabric 704 about the outer and inner openings 706,708, good tissue ingrowth is noted.

Manufacturing

In some variations, the stent structure may be manufactured using a super-elastic nitinol tube that is laser cut with various slits and slots to achieve the initial tubular stent shape. Next, in a series of cyclic deformation, heating, and cooling steps, the tubular stent is expanded stepwise to at least the initial size of the inner lumen of the stent structure. Then the portion of the stent structure corresponding to the transition wall and outer wall are than further expanded stepwise to the desired diameter, and followed by the a stepwise eversion to form the outer wall using a mandrel, and a stepwise reduction of the middle region of the outer wall, or further expansion of the upstream and downstream end regions of the outer wall, is performed to achieve the reduce diameter shape of the outer wall. In another step, one or more bend regions on the lateral struts about the middle region are radially displaced outward to form the retention barbs or structures.

In an alternate embodiment, after initial cutting the tube, the tube may undergo a series of cyclic deformation, heating, and cooling steps, to expand the tube in a stepwise manner to at least the initial size of the outer lumen of the stent structure, then the portion of the stent structure corresponding to the transition wall and inner wall are then inverted into the outer wall to form the closed end and the inner wall. The outer wall may be further expanded or adjusted stepwise to the desired shape, e.g. by further expanding the open and closed end regions of the outer wall, or by reducing the cross-sectional size or diameter of the middle region. One or more bend regions on the lateral struts about the middle region may also be radially displaced outward to form the retention barbs or structures Valve Loading and Delivery As noted previously, a plurality of control apertures may be provided on stent structure, which may be used to attach one or more sutures to control the expansion and contraction of different regions on the stent structure, and/or one or more hooks to releasably retain the stent structure until final deployment at the treatment site. In other examples, rather than using a control aperture, a suture or wrap may be provided over the exterior of one or more regions of the stent structure.

In some examples, the sutures may be tensioned or cinched to collapse the outer and inner walls of the stent structure, for loading onto the delivery catheter. The sutures may be manipulated to collapse inner wall first, before the outer wall, or may collapse both simultaneously. Similarly, one end of the inner wall or outer wall may be collapsed first, or both ends of the inner wall or outer wall may be collapsed simultaneously. This may be done at room temperature, or in a sterile cold or ice water bath at the point of use or at the point of manufacture. After collapse, a sheath may be extended distally over the distal catheter portion where the replacement valve resides. The valve may also be rinsed in sterile saline before loading to remove any remaining preservative on the valve.

In some variations, the transition wall of the stent structure folds down at the inner junction such that in the collapsed configuration, the transition wall is positioned directly over the delivery catheter or tool, like the inner wall, but in other examples, the outer wall is pulled distally during collapse and loading, and unfolds the transition wall at the outer junction, such as the transition wall is located radially outward from the inner wall when contracted into the collapsed configuration.

The retaining sutures of the delivery system may be controlled proximally by the user with pulling rings, sliding levers, and/or rotating knobs, which are further configured to lock into place except during movement via bias springs or mechanical interfit locking configurations as known in the art. The proximal end of the delivery system may also be controlled robotically, using any of a variety of robotic catheter guidance systems known in the art. The sutures may slide along one or more interior lumens of the delivery catheter, in addition to any flush lumen, guidewire lumen, or steering wire lumen(s) provided, including rapid exchange guidewire configurations. The sutures may exit at different locations about the distal region of the delivery catheter, and may exit about the distal region of the catheter via multiple openings. The multiple openings may be spaced apart around the circumference of the catheter body and/or spaced apart longitudinally, depending on the region of the stent structure controlled by sutures.

In one exemplary method of delivering the replacement valve, the patient is positioned on the procedure table, and the draped and sterilized in the usual fashion. Anesthesia or sedation is achieved. Percutaneous or cutdown access to the femoral vein is obtained and an introducer guidewire is inserted. A guidewire is manipulated to reach the right atrium and then a Brockenbrough needle is positioned and used to puncture the interatrial septum to achieve access to the left atrium. Alternatively, image guidance may be used to detect whether a patent septum ovale or remnant access is available, and the guidewire may be passed through the pre-existing anatomical opening. A balloon catheter may also be used as need to enlarge the opening across the intra-atrial septum. An electrocautery catheter may also be used to form an opening in the intra-atrial septum. Once in the left atrium, the guidewire is passed through the mitral valve and intro the left ventricle. Pre-shaped guidance catheters or balloon catheters may be used to facilitate the crossing of the mitral valve. Once in the left ventricle, the delivery catheter with the replacement valve is inserted over the guidewire.

Referring to FIG. 8A, the delivery system 800 with the delivery catheter 802 and valve 804 is positioned across the mitral valve opening 806. The delivery system 800 may also be further manipulated to adjust the angle of entry through the mitral valve opening 806 to be roughly orthogonal to the native valve opening and/or to be centered with the mitral valve opening 806. Once the desired catheter pose is achieved, the delivery sheath 808 is withdrawn proximally, to expose the collapsed valve 804.

In FIG. 8B, the set of sutures controlling the release of the downstream or ventricular end 810 of the outer wall 812 of the valve 804 is partially released, while the tension members controlling the inner wall 816 remains tensioned. Next, in FIG. 8C, ventricular end 810 of the outer wall 812 of the valve 804 is further released, allowing the ventricular end, the middle region and more of the atrial end 814 of the outer wall 812 to expand further, thereby allowing the transition wall 816 of the valve 802 to at least partially expand outward. The partial expansion of the atrial end 814 and the ventricular end 810 of the valve 802 helps to further center and orient the middle region 822 of the valve 802 orthogonally prior to complete release. While the initial expansion of the atrial end 814 of the outer wall 812 in this embodiment is a secondary effect from the partial release of the ventricular end 810 of the valve 802 as longitudinal tension is released, in other examples, independent tension member control of the atrial end 814 may be provided.

Figures 8D, 8E:
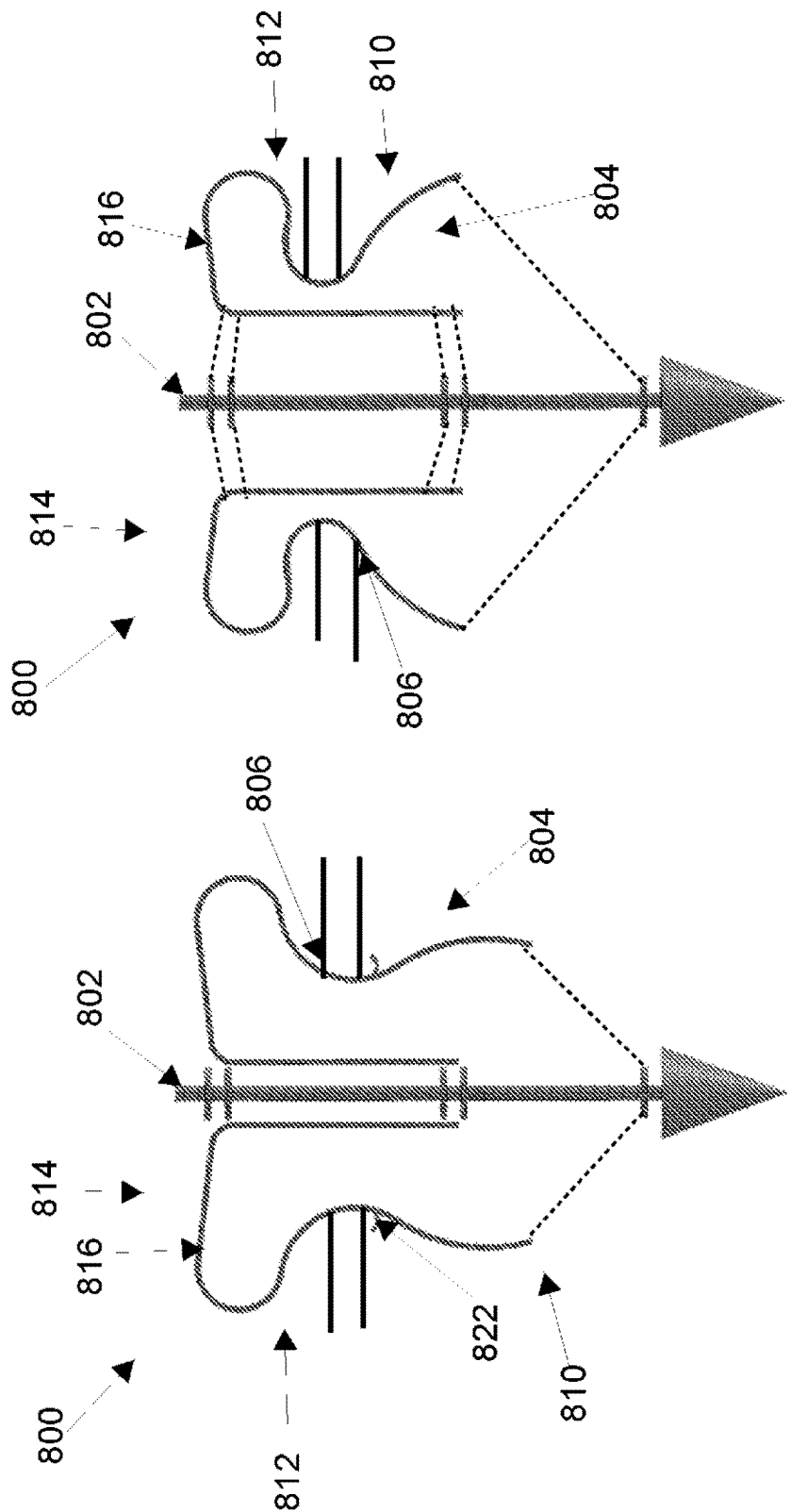

In FIG. 8D, the tension members of the ventricular end 810 and atrial end 814 are further released, either simultaneously or singly in a stepwise fashion, further engaging the middle region 820 of the outer wall 812 against the valve opening 806. This further expansion of the outer wall 812 also exposes the retention barbs or projections 822 on the outer wall 812. Proper centering and orientation of the valve is reconfirmed, to make sure the valve has not been deployed in a skewed or partially disengaged pose with respect to the mitral valve annulus. In some variations, the tension members may be re-tensioned to re-collapse the valve 804 may be performed, to facilitate re-positioning and/or re-orienting of the valve 804. Once confirmed, the tension members of the inner wall 818 may be released, as shown in FIG. 8E, which also allows the outer wall 812 to achieve its untethered expansion against the mitral valve opening 806. The tension members can then be cut or otherwise released or separated from the valve and the tension members may be withdrawn into the catheter and optionally out of the proximal end of the catheter. The delivery catheter and guidewire can then be withdrawn from the patient and hemostasis is achieved at the femoral vein site.

In one exemplary method of delivering the replacement valve, the patient is positioned on the procedure table, and the draped and sterilized in the usual fashion. Anesthesia or sedation is achieved. Percutaneous or cutdown access to the vascular or entry site is obtained, e.g. at the femoral vein, femoral artery, radial artery, subclavian artery, and an introducer guidewire is inserted. A guidewire is manipulated to reach the desired valve implantation site. Pre-shaped guidance catheters or balloon catheters may be used to facilitate the crossing of the valve implantation site Referring to FIG. 8A, the delivery system 800 with the delivery catheter 802 and valve 804 is positioned across the valve opening 806. The delivery system 800 may also be further manipulated to adjust the angle of entry through the valve opening 806 to be roughly orthogonal to the native valve opening and/or to be centered with the valve opening 806. Once the desired catheter pose is achieved, the delivery sheath 808 is withdrawn proximally, to expose the collapsed valve 804.

In FIG. 8B, the set of tension members controlling the release of the downstream end 810 of the outer wall 812 of the valve 804 are partially released, while the tension members controlling the inner wall 816 remain tensioned. Next, in FIG. 8C, downstream end 810 of the outer wall 812 of the valve 804 is further released, allowing the downstream end, the middle region and more of the upstream end 814 of the outer wall 812 to expand further, thereby allowing the transition wall 816 of the valve 802 to at least partially expand outward. The partial expansion of the atrial end 814 and the ventricular end 810 of the valve 802 helps to further center and orient the middle region 822 of the valve 802 orthogonally prior to complete release. While the initial expansion of the atrial end 814 of the outer wall 812 in this embodiment is a secondary effect from the partial release of the ventricular end 810 of the valve 802 as longitudinal tension is released, in other examples, independent tension member control of the upstream end 814 may be provided.

In FIG. 8D, the tension members of the downstream end 810 and upstream end 814 are further released, either simultaneously or singly in a stepwise fashion, further engaging the middle region 820 of the outer wall 812 against the valve opening 806. This further expansion of the outer wall 812 also exposes the retention barbs or projections 822 on the outer wall 812. Proper centering and orientation of the valve is reconfirmed, to make sure the valve has not been deployed in a skewed or partially disengaged pose with respect to the valve annulus. The tension members may be optionally re-tensioned to re-collapse the valve 804 may be performed, to facilitate re-positioning and/or re-orienting of the valve 804. Once confirmed, the tension members of the inner wall 818 are released, as shown in FIG. 8E, which also allows the outer wall 812 to achieve its untethered expansion against the mitral valve opening 806. The tension members can then be separated from the valve 804 and withdrawn into the catheter and optionally out of the proximal end of the catheter 802.

In still another exemplary method of delivering the replacement valve, the patient is positioned on the procedure table, and the draped and sterilized in the usual fashion. Anesthesia or sedation is achieved, with selective ventilation of the right lung and optionally the left upper lobe of the lung to permit controlled collapse of the left lower lobe of the lung. A pursestring suture is placed at the transapical or other cardiac entry site. A trocar is inserted through a cannula or introducer with a proximal hemostasis valve, and the trocar assembly is inserted through the pursestring suture to access the cardiac chamber and the target valve.

Referring to FIG. 8A, the delivery system 800 with the delivery rigid tool 802 and valve 804 is positioned across the valve opening 806. The delivery system 800 may also be further manipulated to adjust the angle of entry through the valve opening 806 to be roughly orthogonal to the native valve opening and/or to be centered with the valve opening 806. Once the desired tool pose is achieved, the delivery sheath 808, if any, is withdrawn proximally, to expose the collapsed valve 804.

In FIG. 8B, the tension members controlling the release of the downstream end 810 of the outer wall 812 of the valve 804 are partially released, while the sutures controlling the inner wall 816 remains tensioned. Next, in FIG. 8C, downstream end 810 of the outer wall 812 of the valve 804 is further released, allowing the downstream end, the middle region and more of the upstream end 814 of the outer wall 812 to expand further, thereby allowing the transition wall 816 of the valve 802 to at least partially expand outward. The partial expansion of the atrial end 814 and the ventricular end 810 of the valve 802 helps to further center and orient the middle region 822 of the valve 802 orthogonally prior to complete release. While the initial expansion of the atrial end 814 of the outer wall 812 in this embodiment is a secondary effect from the partial release of the ventricular end 810 of the valve 802 as longitudinal tension is released, in other examples, independent suture control In FIG. 8D, the tension members of the downstream end 810 and upstream end 814 are further released, either simultaneously or singly in a stepwise fashion, further engaging the middle region 820 of the outer wall 812 against the valve opening 806. This further expansion of the outer wall 812 also exposes the retention barbs or projections 822 on the outer wall 812. The tension members may be optionally re-tensioned to re-collapse the valve 804 may be performed, to facilitate re-positioning and/or re-orienting of the valve 804. Proper centering and orientation of the valve is reconfirmed, to make sure the valve has not been deployed in a skewed or partially disengaged pose with respect to the valve annulus. Once confirmed, the tension members of the inner wall 818 are released, as shown in FIG. 8E, which also allows the outer wall 812 to achieve its untethered expansion against the mitral valve opening 806. The suture lines can then be cut and the cut ends withdrawn into the catheter and optionally out of the proximal end of the delivery tool 802.

While the embodiments herein have been particularly shown and described with references to embodiments thereof, it will be understood by those skilled in the art that various changes in form and details may be made therein without departing from the scope of the embodiments. For all of the embodiments described above, the steps of the methods need not be performed sequentially.

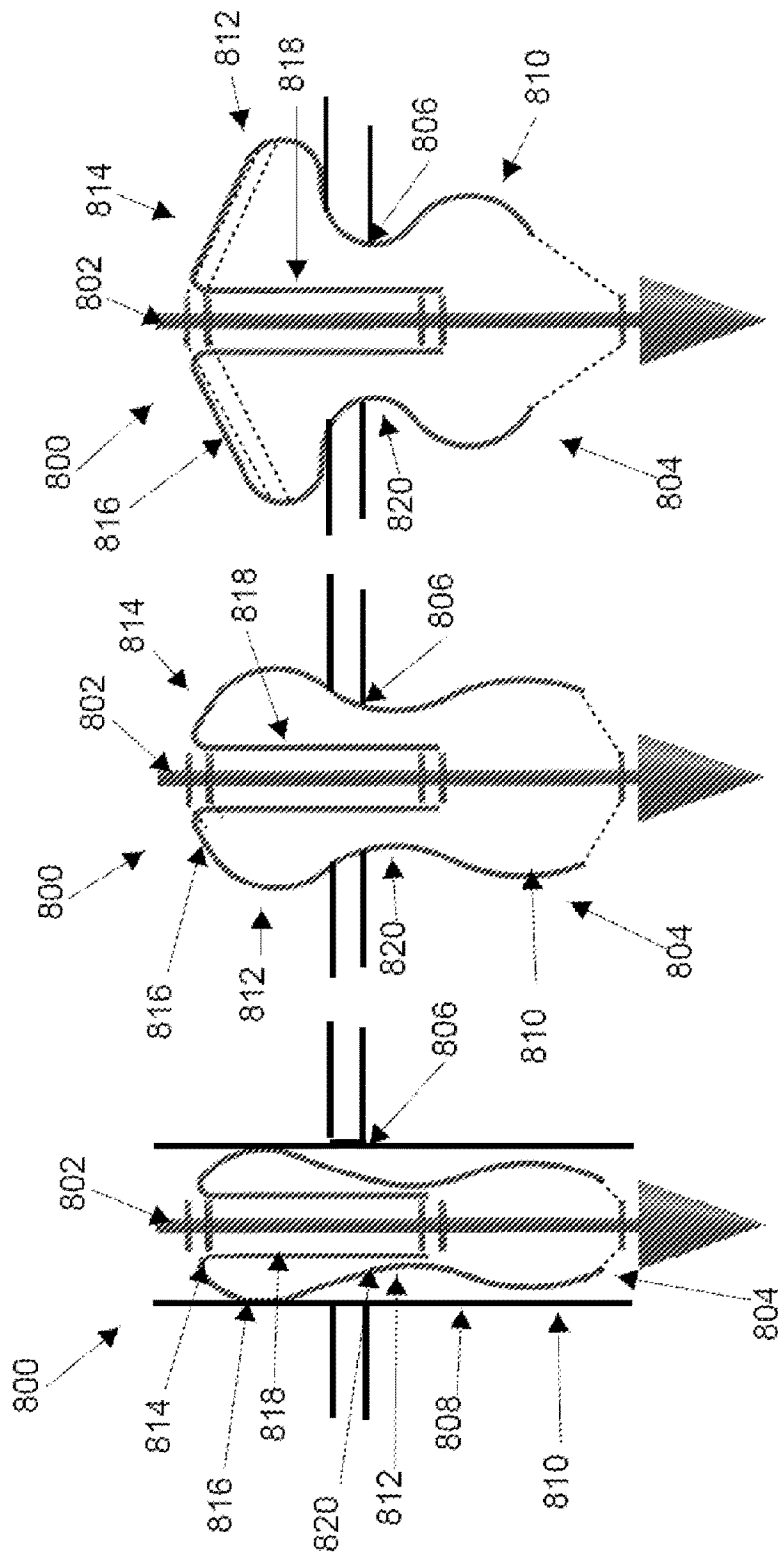

What is claimed is:

1. A replacement heart valve, comprising:
   a unibody stent frame with a folded double-wall, the stent frame comprising:
   a collapsed configuration and an expanded configuration;
   an outer wall comprising a downstream open enlarged diameter region, a middle reduced diameter region, and an upstream closed enlarged diameter region;
   a tubular inner wall with a central lumen;
   a transition wall between the upstream closed enlarged diameter region of the outer wall and the inner wall; and
   a first radius of curvature $R_1$ between the inner wall and the transition wall, a second radius of curvature $R_2$ between the transition wall and the outer wall, and a third radius of curvature $R_3$ at the middle reduced diameter region, wherein $R_1<R_2<R_3$; and
   a replacement leaflet valve located in the central lumen of the inner wall;
   wherein the unibody stent frame further comprises a plurality of longitudinal struts, wherein each longitudinal strut is contiguously located along the inner wall, transition wall and outer wall; and
   wherein the plurality of longitudinal struts are integrally formed with a plurality of circumferential struts.

2. The valve of claim 1, wherein the unibody stent frame further comprises a first curvature between the closed enlarged diameter region and the tubular inner wall.

3. The valve of claim 2, wherein the unibody stent frame comprises a second curvature between the closed enlarged region and the open enlarged region.

4. The valve of claim 3, wherein a radius of curvature at the first curvature is smaller than a radius of curvature at the second curvature.

5. The valve of claim 1, wherein the outer wall surrounds at least 70 percent of the inner wall in the expanded configuration.

6. The valve of claim 5, wherein the outer wall and transition wall completely surrounds the inner wall in the collapsed configuration.

7. The valve of claim 1, wherein the tubular inner wall comprises a non-foreshortening region surrounding the replacement valve, when transitioning from the collapsed configuration to the expanded configuration.

8. The valve of claim 1, wherein the inner wall is a non-foreshortening inner wall, and the outer wall is a foreshortening outer wall.

9. The valve of claim 1, wherein for at least one of the plurality of longitudinal struts, contiguous segments of the longitudinal strut located in the inner wall, transition wall and outer wall are co-planar.

10. The valve of claim 9, wherein the contiguous segments of the longitudinal strut are also co-planar with a central longitudinal axis of the unibody stent frame.

11. The valve of claim 1, wherein at least three circumferential struts are located in the outer wall.

12. The valve of claim 1, further comprising a stent covering, the stent covering comprising:
a first region on an outer surface of the outer wall;
a second region on an open end of the outer wall;
a third region on an outer surface of the transition wall;
a fourth region on an inner surface of the inner wall;
a fifth region on an open end of the inner wall;
a sixth region on an outer surface of the inner wall;
a seventh region on an inner surface of the outer wall; and
an eighth region portion between the inner surface of the outer wall and the outer surface of the inner wall.

13. The valve of claim 12, wherein:
the first, second, third, and a portion of the fourth regions comprise a first fabric structure;
a portion of the fourth region and the fifth region comprises a second fabric structure; and
the sixth, seventh and eighth regions comprise a third fabric structure.

14. The valve of claim 13, wherein the first fabric structure and the third fabric structure comprise a first fabric material and the second fabric structure comprises a second fabric material different from the first fabric material.

15. The valve of claim 14, wherein the first fabric material is less permeable and thinner than the second fabric material.

16. The valve of claim 1, wherein the stent frame further comprises a fourth radius of curvature $R_4$ at the downstream open enlarged diameter region of the outer wall.

17. The valve of claim 16, wherein $R_3 \leq R_4$.

18. The valve of claim 1, wherein:
the stent frame further comprises a first bend angle $A_1$ between the inner wall and the transition wall, a second bend angle $A_2$ between the transition wall and the outer wall, and a third bend angle $A_3$ at the middle reduced diameter region; and
$A_3 > A_a$.

19. The valve of claim 18, wherein $A_3 > A_2$.

20. The valve of claim 19, wherein:
the stent frame further comprises a fourth bend angle $R_4$ at the downstream open enlarged diameter region of the outer wall; and
$A_3 > A_4$.

* * * * *

UNITED STATES PATENT AND TRADEMARK OFFICE
CERTIFICATE OF CORRECTION

| | | |
|---|---|---|
| PATENT NO. | : 11,197,755 B1 | |
| APPLICATION NO. | : 17/083266 | |
| DATED | : December 14, 2021 | |
| INVENTOR(S) | : Daniel T. Wallace et al. | |

It is certified that error appears in the above-identified patent and that said Letters Patent is hereby corrected as shown below:

In the Drawings

Delete Figures 8A, 8B, and 8C and replace with the attached drawing sheet showing the corrected figures.

Delete Figures 8D and 8E and replace with the attached drawing sheet showing the corrected figures.

Signed and Sealed this
Eleventh Day of October, 2022

*Katherine Kelly Vidal*

Katherine Kelly Vidal
*Director of the United States Patent and Trademark Office*